US008438042B2

(12) United States Patent
Ledley

(10) Patent No.: US 8,438,042 B2
(45) Date of Patent: May 7, 2013

(54) INSTRUMENTS AND METHODS FOR OBTAINING INFORMED CONSENT TO GENETIC TESTS

(75) Inventor: Fred David Ledley, Needham, MA (US)

(73) Assignee: National Biomedical Research Foundation, Bethesda, MD (US)

( * ) Notice: Subject to any disclaimer, the term of this patent is extended or adjusted under 35 U.S.C. 154(b) by 2377 days.

(21) Appl. No.: 10/134,424

(22) Filed: Apr. 25, 2002

(65) Prior Publication Data

US 2003/0204418 A1    Oct. 30, 2003

(51) Int. Cl.
G06F 17/60 (2006.01)
(52) U.S. Cl.
USPC .......... 705/3; 600/300; 379/265.01; 434/322; 702/20; 702/179; 702/84
(58) Field of Classification Search .................. 705/2–3; 600/300; 379/265, 265.01; 364/400; 434/322
See application file for complete search history.

(56) References Cited

U.S. PATENT DOCUMENTS

| | | | |
|---|---|---|---|
| 5,757,917 A | | 5/1998 | Rose et al. |
| 5,876,926 A | | 3/1999 | Beecham |
| 5,978,466 A | * | 11/1999 | Quattrocchi ............. 379/265.01 |
| 5,999,909 A | * | 12/1999 | Rakshit et al. ..................... 705/2 |
| 6,018,713 A | * | 1/2000 | Coli et al. .......................... 705/2 |
| 6,055,487 A | | 4/2000 | Margrey et al. |
| 6,141,653 A | | 10/2000 | Conklin et al. |
| 6,149,440 A | * | 11/2000 | Clark et al. .................... 434/322 |
| 6,192,320 B1 | | 2/2001 | Margrey et al. |
| 6,287,254 B1 | | 9/2001 | Dodds |
| 6,523,009 B1 | * | 2/2003 | Wilkins ............................. 705/3 |
| 6,874,085 B1 | * | 3/2005 | Koo et al. ...................... 713/165 |
| 2002/0007285 A1 | * | 1/2002 | Rappaport ........................ 705/2 |
| 2002/0187483 A1 | | 12/2002 | Hoffman et al. |
| 2004/0029138 A1 | * | 2/2004 | Allan et al. ........................ 435/6 |

OTHER PUBLICATIONS

Advisory Committee on Genetic Testing Code of Practice and Guidance on Human Genetic Testing Services Supplied Direct to the Public by John Polkinghorne KBE FRS, Aug. 1997).*
Advisory Committee on Genetic Testing Code of Practice and Guidance on Human Genetic Testing Services Supplied Directly to the Public by John Polkingham (Sep. 1997).*
"Attachment to AHA Regulatory Advisory: Model HOPPA notice of privacy practices," Feb. 13, 2001.
"GeneScreen: bonemarrowtest.com" www.genescreen.com/bone_marrow_testing.asp, printed Dec. 11, 2001, 4 pages.
Perr I. N., "Privilege, confidentiality and patient privacy: status 1980," *J. Forensic Sci.* 26:109-115 (1981).
Williams-Jones, "Re-framing the discussion: Commercial genetic testing in Canada,"*Health Law Journal* (Canada) 7:49-67 (1999).
Yan et al., "Genetic testing—present and future," *Science* 289(5486):1890-1892 (2000).
McKinnon et al, The Familial cancer program of the Vermont Cancer Center: Development of a cancer genetics program in a rural area. Journal of Genetic Counseling, 6(2): 131-145, 1997.
Tarczy-Hornoch et al., "Creation and Maintenance of Helix, a Web Based Database of Medical genetics Laboratories, to Serve the Needs of the Genetics Community", Proc AMIA Symp (1998) pp. 1-5.
Non-Final Office Action dated Apr. 5, 2012 in related U.S. Appl. No. 13/205,556.
Attachment to AHA Regulatory Advisory: Model HOPPA notice of privacy practices. Feb. 13, 2001.
Examiner's Answer dated Jul. 20, 2009 from related U.S. Appl. No. 10/200,978.
Office Action dated Apr. 1, 2005 from related U.S. Appl. No. 09/630,631.
Office Action dated Apr. 17, 2009 from related U.S. Appl. No. 09/630,631.
Office Action dated Aug. 1, 2005 from related U.S. Appl. No. 09/630,631.
Office Action dated Aug. 19, 2005 from related U.S. Appl. No. 10/200,978.
Office Action dated Aug. 26, 2003 from related U.S. Appl. No. 09/630,631.
Office Action dated Dec. 10, 2007 from related U.S. Appl. No. 10/200,978.
Office Action dated Feb. 10, 2006 from related U.S. Appl. No. 10/200,978.
Office Action dated Feb. 26, 2007 from related U.S. Appl. No. 10/200,978.
Office Action dated Dec. 4, 2001 from related U.S. Appl. No. 09/630,631.
Office Action dated Feb. 5, 2010 from related U.S. Appl. No. 09/630,631.
Office Action dated Feb. 8, 2006 from related U.S. Appl. No. 09/630,631.
Office Action dated Feb. 7, 2008 from related U.S. Appl. No. 09/630,631.
Office Action dated Jul. 13, 2006 from related U.S. Appl. No. 09/630,631.
Office Action dated Jul. 6, 2006 from related U.S. Appl. No. 10/200,978.
Office Action dated Jun. 14, 2007 from related U.S. Appl. No. 09/630,631.
Office Action dated Mar. 4, 2005 from related U.S. Appl. No. 10/200,978.
Office Action dated May 20, 2004 from related U.S. Appl. No. 09/630,631.

(Continued)

*Primary Examiner* — Vanel Frenel
(74) *Attorney, Agent, or Firm* — Foley & Lardner LLP

(57) ABSTRACT

This invention provides an instrument for obtaining consent for a genetic test that comprises three or more integrated elements including an information element for conveying information to an individual concerning a genetic test, and instruction element for use by a practitioner in instructing individuals on the genetic test and use of the instrument, a collection element for collecting an individual's medical and family history, a assessment element for assessing the individual's retention and understanding of information concerning a genetic test, a certification element for certifying the individual's consent to said tests, as well as housekeeping elements useful for recording a medical record, labeling a sample, and billing. Also provided is a method for obtaining informed consent for a genetic test using an integrated instrument. The instruments and methods disclosed have utility in obtaining informed consent for genetic tests.

17 Claims, No Drawings

OTHER PUBLICATIONS

Office Action dated Nov. 17, 2006 from related U.S. Appl. No. 09/630,631.
Office Action dated Sep. 17, 2008 from related U.S. Appl. No. 10/200,978.
Perr I.N., Privilege, confidentiality and patient privacy: status 1980, J. Forensic Sci, 26:109-115 (1981).
Tarczy-Hornoch, et al, Creation and maintenance of helix, a web based database of medical genetics labaoratories, to serve the needs of the genetics community, (1998), Proc AMIA Symp, pp. 1-5.
Williams-Jones, Re-framing the discussion: Commercial genetic testing in Canada, Health Law Journal (Canada) 7:49-67 (1999).
Yan et al., Genetic testing—present and future, Science 289(5486):1890-1892 (2000).
U.S. Office Action for U.S. Appl. No. 09/630,631, dated Apr. 17, 2009.
Decision of the Patent Trial and Appeal Board in related U.S. Appl. No. 09/630,631 (Appeal No. 2011-006312) issued Nov. 19, 2012.

* cited by examiner

INSTRUMENTS AND METHODS FOR OBTAINING INFORMED CONSENT TO GENETIC TESTS

FIELD OF THE INVENTION

This invention provides novel instruments and methods for obtaining informed consent for genetic tests.

BACKGROUND OF THE INVENTION

The human genome project has been undertaken with the expectation that the sequences of genes that comprise the genome are determinants of individual development, health, and disease. Variation in gene sequences, variations in the level, location, or timing of expression of a gene, and variation in the physical, chemical, or dynamic characteristics of the products expressed from a gene are known to underlie many aspects of human individuality including physical and mental characteristics, growth, longevity, health, and disease. An objective of genomic research is the discovery, development and implementation of genetic tests that can be used to determine how the genes of an individual predispose that individual to various clinical outcomes. Genetic tests are expected to have a central role in routine health, wellness, and disease management, enabling predisposition testing and interventions to prevent disease, providing early diagnosis, and optimizing pharmacological interventions with drugs that are likely to be safe and effective for an individual.

The utilization of genetic tests and the interpretation of genetic tests results are more complex than conventional diagnostic testing. The number of genetic tests that will be available from human genomic research is very large compared to the number of conventional diagnostic tests. The genome project is expected to reveal 30,000-100,000 genes and >10,000,000 discrete genetic variations that may be developed into genetic tests with utility in predicting specific health outcomes. Few individuals or healthcare practitioners are familiar with the many genes different already known to be associated with specific health outcomes. Few have the ability to remain current with the rapidly emerging literature in this field. The effective and ethical use of genetic tests requires that individuals have sufficient information about the tests to decide whether to have the test done and to make efficacious use of the test result. This requires that individuals have access to information concerning the potential benefits of genetic testing, the procedures involved in genetic testing, and the potential risks to health and privacy. Because of the unique nature of genetic testing, good medical practice and statutory requirements in some states require that an informed consent be obtained from an individual before a sample is obtained and a genetic test is performed. To provide a valid informed consent, an individual must have been given and must retain and understand sufficient information concerning the test, the DNA sample, the potential use of genetic information that may be obtained from the sample, and the potential benefits and risks associated with the test to make an informed decision regarding the test.

Genetic testing is typically initiated by health care practitioners (including primary or subspecialty physicians or practitioners specialized in genetics, such as MD, PhD, or MA/MS trained geneticists or genetic counselors), and informed consent is obtained by the practitioner during a meeting with the individual. During this meeting, the practitioner must provide the individual with information sufficient for the individual to make an informed choice and to certify their consent to the testing procedure. After certification, samples are typically obtained by the health care practitioner or a designated blood drawing facility and tests are then performed by certified laboratories. The test result is reported from the laboratory to the practitioner and/or to the individual. Many practitioners do not have sufficient training in genetics, knowledge relating to individual genetic tests, or time to adequately provide individuals with the information required to provide a legally binding informed consent.

The process of obtaining informed consent is described in many textbooks, articles, reports, and recommendations. In current practice, information about genetic tests is collected by practitioners and individuals from a variety of sources including textbooks of medicine or genetics, as well as articles in medical journals, courses for continuing medical education, government agencies, disease advocacy groups, biotechnology companies, academic research groups, the Internet, and articles in the lay press. This information, as well as information about the process of obtaining a genetic test, and the use of genetic test results is discussed with the individual in an ad hoc manner. Many sources of information are written at a level appropriate for healthcare practitioners. Few are appropriate for individuals in the general public. Moreover, information gleaned from multiple sources is often conflicting and incomplete. Few sources of information are validated in clinical studies to demonstrate that the content and mode of presentation results in comprehension and retention by the individual.

Documents by which an individual can certify their consent to a genetic test are known in the art. Such documents focus primarily on legal issues related to genetic testing such as the technical and predictive limitations of genetic testing, potential errors in diagnosis and interpretation, the disposition of the DNA sample, and the reporting of test results. Informed consent documents are typically generic, i.e., they address issues that are relevant to many different genetic tests and clinical outcomes rather than being specific to particular genetic test, genetic tests for related genes, or a specific clinical outcome.

Because of the complexity of genetic information, the widespread lack of professional training in genetics and procedures for delivering genetic services, and the lack of validated resources for providing genetic services, surveys suggest that <10% of practitioners feel that they are capable of adequately providing such services. Moreover, despite laws in some states that require informed consent be obtained before genetic tests are performed, data demonstrates that many genetic tests are performed without any informed consent being obtained or with inadequate informed consent.

SUMMARY OF THE INVENTION

The inventor has determined that an instrument for obtaining informed consent comprising integrated elements with information for the individual, instruction for the practitioner, and materials for certifying an individual's consent and, optionally, elements for processing the genetic record, sample collection, and billing has utility in assisting practitioners to obtain meaningful and legally binding informed consent. This instrument may be validated to establish that it is effective in establishing understanding, comprehension, and effective use of the test and test result. The instrument described in this invention provides an individual with information about a genetic test for one gene, more than one gene, related genes, genes associated with a clinical outcome or for a gene screen and assists the provider in obtaining a valid informed consent and performing other procedures associated with genetic testing.

The instrument comprises an information element, an instruction element and a certification element. The elements are integrated. The information element contains information sufficient for an individual to provide a valid informed consent. This element is integrated with an instructional element for the practitioner that contains more detailed reference information on the gene, gene test, or clinical outcome that is the subject of the test as well as stepwise directions on how to instruct the individual in the information in the information element and materials designed to support such instruction. The integrated instrument contains both informational materials required by the practitioner and the individual as well as worksheets, checklists, forms, illustrative materials and other materials required to carry out these steps in an integrated manner. The information element contains basic information for individuals about the genetic test including text and illustrative materials in the primary language of the individual and at a level of comprehension appropriate for the general population. It is generally considered that materials intended for comprehension by the general population should not exceed an 8-10$^{th}$ grade level. The information element is designed to provide individuals with information that is accurate, timely, and useful and considered by experts to be sufficient for an individual to make an informed decision to proceed with a genetic test. The information element may contain illustrative materials as well as supplemental information about genetics, genetic tests, or a clinical outcome, or references or links to more advanced information available in printed materials or electronic medium.

The instruction element directs the practitioner how to present information to individuals and how to obtain informed consent using the instrument. This element includes stepwise instructions on the use of the instrument and each of the elements comprising the instrument, reference information at the level of the practitioner on medical genetics, the genetic test, and related clinical outcomes, and answers to questions that are frequently asked by individuals during the consent process. The instruction element preferably contains a checklist to document that the practitioner has followed each of the steps required for use of the instrument. The instruction element may contain illustrative materials for use by the practitioner in presenting information to the individual, for example, props, diagrams, worksheets, objects, exercises, questions, or games that can be used to improve the individuals retention and comprehension of the information. The instruction element may also include a worksheet to assist the practitioner in calculating an individual's genetic risk of a clinical outcome based on genetic test results as well as information from the individual's medical history or family history.

The instruction element advantageously reduces the impact of the practitioner's subjectivity. It is well known that, for example, validated instruments for neuro-psychological testing require the practitioner to adhere strictly to the instruction set in order achieve valid testing results. In this invention, the instruction element provides the means for standardization of the procedures employed by the practitioner in obtaining informed consent, and enables consent to be obtained in a validated manner. In addition, it is generally recognized that information presented to individuals and the practices of the practitioner should be non-directive. The standardized and validated information element and instruction elements minimize unintentional bias and improve the quality and ethics of the consent and the consent process.

The instrument of this invention also includes a certification element. The certification element comprises a legal document in which the individual consents to the genetic test before any required witnesses, who certify that the individual has consented to the genetic test.

Optionally included in the instruments of the invention are various other elements, to wit, an assessment element, a collection element, a labeling element, a billing element, a recording element, a training element, a quality control element and an indemnification element. One or any more than one of these elements may be included with the information, the instruction and the certification elements that comprise the instrument of the invention. Preferred elements to be included comprise the assessment element or the collection element, or both. Any optional element included in the instrument is integrated with one or more of the three essential elements.

The assessment element assesses the individual's retention and understanding of information contained in the information element and instruction element. The assessment element comprises questions about the genetic test, the risks and benefits of the test, clinical practice guidelines, recommendations, and possible clinical actions in response to the test results. The assessment element is integrated with the information element, in that the questions in the assessment element concern content from the information element, as well as the instruction element, which provides correct answers to each of the questions and procedures for responding to incorrect questions. The assessment element is intended to determine whether the individual satisfies the minimum standards of retention and understanding sufficient to provide a valid informed consent. The assessment also serves as an internal form of quality control on the ability of the practitioner to practice this method.

The integrated collection element assists the provider in obtaining information from an individual concerning their personal medical history and family history that is useful in deciding whether or not to have a genetic test performed and quantitatively determine the individual's genetic risk. This element is integrated with the information element which describes, for example, how an individual's family history impact their risk of a clinical outcome, as well as the instruction element which provides the practitioner with the ability to collect the personal medical history and family history and analyze this information to make a preliminary assessment of risk.

The other optional elements provide "housekeeping" functions. The labeling element and the billing element further assists the practitioner in processing the sample for genetic testing, establishing a genetic record, and obtaining payment for the test. The recording element ensures that a record of the informed consent process and the certification is established. The training element trains practitioners in the use of the instrument, the quality control element assesses the performance of the user against performance standards, and the indemnification element provides an indemnification form for practitioners who use the instrument to obtain consent against claims that adequate informed consent was not properly obtained.

The method described in this invention involves the use of an integrated instrument to obtain valid informed consent. This method comprises, briefly, the steps of transmitting to the individual information on the genetic test and on the process of testing, instructing the individual with respect to the genetic test and the testing process and obtaining the individual's certified consent to the test using an integrated instrument. The method may optionally include the steps of collecting a personal medical history and family history using an integrated collection element, assessing the individual's retention or comprehension of this information using an integrated assessment element, labeling the sample with information required for proper sample handling using an integrated labeling element, and recording information concerning the informed consent process, the test to be performed, and the individual's medical and family history in a medical record using an integrated recording element. The method preferably includes the two steps of collecting and/or assessing. It may include any one or more of the remaining steps of labeling, billing training, providing quality control, indemnification and recording using integrated elements. Preferably these steps are performed using integrated elements.

One or more of the elements of the instrument may be posted to make it generally available to individuals or practitioners, by placing it on a web site, and providing it as a resource in printed or electronic medium accessible to individuals or practitioners, or incorporating it in policies, practices, guidelines, recommendations, training materials, or lessons and using integrated elements for one or more of the steps of informing, instructing, assessing, collecting, certifying, labeling, and recording. Preferably the information element and/or the instruction element is posted.

DETAILED DESCRIPTION OF THE INVENTION

A. Definitions and General Information

"Genetic test", "gene test", "test", or "genetic testing" mean the analysis of DNA, RNA, protein, or other biological materials in a sample from an individual to determine, without limitation, the sequence or structure of one, or more than one, gene, the presence or absence of one, or more than one, genetic marker, variance, variation, mutation, polymorphism, or micro satellite sequence associated with a gene, the presence of one, or more than one, viral sequence, viral-like sequence, or repetitive sequence, a haplotype or genotype spanning one, or more than one, gene, the number of copies of one, or more than one, gene, the amount or characteristics of RNA or protein expressed from one, or more than one, gene, the biological function of one, or more than one, gene, the arrangement of genes within the genome, the chromosome number, or integrity, modification, or structure of DNA and chromosomes. Many gene tests are useful in medicine for determining and individual's risk of a clinical outcome including diagnosing genetic disease, determining an individual's propensity to multifactorial diseases, and/or predicting an individual's response to therapeutic drugs. Genetic tests have been developed for many inherited diseases including, for example, Huntington's Disease, Cystic Fibrosis, and Phenylketonuria. Genetic tests have also been developed for genes that predispose to common, multifactorial diseases including, for example, atherosclerosis, heart failure, stroke, anemia, cancer, clotting disorders, dementia, endocrine diseases, osteoporosis, and pulmonary diseases. Genetic tests have also been described which predict the pharmacokinetic and pharmacodynamic characteristics of many drugs including, for example, drugs for the treatment of elevated cholesterol, drugs to treat cancer, drugs to reduce hypertension, and drugs to treat dementia. The term genetic test includes any test which determines the structure, characteristics, amount, or activity of certain chemical entities that reflect the structure or function of one gene or more than one gene.

A common form of a genetic test involves the sequencing of one or more genes to determine whether the sequence corresponds to a sequence known to encode a gene product associated with normal biological or clinical activity or having a variant sequence that encodes a gene product that correlates with an abnormal function, disease, or clinical outcome. Gene sequences can be determined from gels, using automated sequencing, gene chips, hybridization to selected or random nucleotide sequences, mass spectroscopy or other methods well known in the art. Methods for selectively determining the sequence of one, or more than one, specific bases within a gene or the sequence of a region of a gene known to be a marker for specific health outcomes or to be associated with specific clinical outcomes are also well known in the art. A genetic test may identify a single variance within a gene or multiple variances within a gene. A genetic test may also identify one or more variances in more than one gene.

One form of a genetic test is a "gene screen" which identifies a large number of variances within one gene or many different genes, potentially every gene in the genome. A gene screen may identify variances in genes that are related through a common pathway, process, or clinical outcome and/or genes that are not related. Such tests raise particularly difficult issues for obtaining informed consent. A specific embodiment of this invention is an instrument for obtaining informed consent for a gene screen. Another common form of genetic test well known in the art quantifies the amount or structure of mRNA for one gene or many different genes in a sample. Other forms of genetic tests involve identification and analysis of specific proteins, or structurally variant forms of proteins by mass spectroscopy, electrophoresis, or by binding to natural or synthetic substrates or antibodies using methods well known in the art.

"Sample" means an aliquot of material from an individual, for example, blood, tissue, hair, skin cells, mucosal cells, or cells from other parts of the body, secretions such as saliva, mucous, urine, feces or other bodily tissues, or fluids, useful for genetic testing. Sample also means DNA, RNA, protein or other chemical entities useful for genetic testing that are extracted or purified from such materials. The term refers to, without limitation, any substance or chemical entity derived directly or indirectly from an individual that contains DNA, RNA, protein, or other materials suitable for performing a genetic test. A sample may contain sufficient material to perform one genetic test or a series of genetic tests over time. The term "label" is generally known in the art and refers to information that is attached to or otherwise associated with a sample or sample collection device which may contain information concerning the handling and disposition of the sample, the test to be performed, and identifying information concerning the individual.

"Sample collection device" is generally known in the art and includes any device for obtaining samples for genetic tests and placing them in a format that can be delivered to the site where the sample can be extracted and the test can be performed. Examples of sample collection devices for genetic testing are known in the art. Sample collection devices may incorporate, for example, filter paper or tubes which hold the sample for transport to a laboratory, extraction of DNA or other components of the sample, storage of the sample, DNA banking, or performing one or more steps of the genetic test. It will be recognized that several difference devices may be used in the course of obtaining and processing a sample and performing a genetic test and storing the sample, and that multiple labels may be required to transmit information through the course of the sample handling and testing procedures. Samples can be collected using routine procedures for blood drawing and commonly employ tubes designed to enable the separation of nucleated cells, plasma or serum. Specialized devices are also known in the art including several devices that are approved by the FDA for sample collection. An exemplary device is the OraSure Oral Specimen Collection Device from Orasure Technologies, Inc. which is an FDA-approved device that can be used for the collection of DNA from the oral mucosa for clinical applications. Another exemplary device is S&S 903 Specimen Collection Paper from Schleicher & Schuell, GmbH which is also a FDA listed device widely used for sample collection, including genetic studies. S&S 903 Specimen Collection Paper, is used widely for newborn screening and has also been used for genetic studies. S&S 903 Specimen Collection Paper has also been incorporated into single and multi-part forms and forms and customized printing is available from the manufacturer with biologically inactive inks and glues that enable the paper to incorporate information or codes for patient identification, processing, and lot traceability. The 903 device can be used to collect blood or body fluids such as urine, tears, or saliva which are spotted and dried onto the 903 paper. In this form the sample is stable and can be mailed to centralized labs for analysis, sample extraction, or DNA banking.

A gene test may be performed using a "diagnostic product" that provides one or more than one of the reagents and materials required to form said test and may include a sample collection device. A diagnostic product typically comprises a kit containing reagents and materials that have been subjected to quality control and premeasured so that the test can be performed effectively by a technician, automated laboratory, or even an individual. Diagnostic products may be reviewed and approved by the Food and Drug Administration as In Vitro Diagnostics. Most genetic testing today is not performed using approved diagnostics, but rather performed under FDA "home brew" guidelines using analyte specific reagents. The term diagnostic product as used herein includes analyte specific reagents, sample collection devices, or other reagents or materials used to perform genetic tests.

"Banking" or "DNA banking" means the storage of a sample intended for future genetic testing. Since the gene sequences of aggregate somatic cells do not change over time (unless the cells are clonal and/or malignant), a sample obtained for one genetic test can be banked and additional tests can be performed at a later time. Informed consent is commonly required for DNA banking. Such consent must describe the potential uses of the sample and the final disposition of the sample. Potential uses may include retesting for quality control, genomic research, or additional tests for the benefit of the individual that may be requested by the individual or practitioner. Such consent should also state whether a sample will be stored indefinitely or destroyed. Preferably the informed consent for a genetic test includes informed consent for banking, the permitted uses of the banked sample in the future, and the disposition of the banked sample.

"Chemical entity" means proteins, protein derivatives (such as glycoproteins, lipoproteins, or phosphoproteins), lipids, carbohydrates, small-molecule organic compounds, and inorganic compounds measured in tissue or body fluids whose structure, activity, characteristics, amount, location, or activity reflects the structure or function of one or more genes. It is recognized that tests on chemical entities often enable direct inferences to be made concerning the structure or activity of one or more genes. For example, electrophoresis of hemoglobin extracted from red blood cells can reveal a change in the hemoglobin molecule caused by the sickle cell mutation in the hemoglobin gene; an increase in the amount of phenylalanine in the blood or urine can reveal the presence of mutations in the gene for phenylalanine hydroxylase; the concentration of salts in sweat can reveal the presence of mutations in the CFTR gene, the ability of a specific monoclonal antibody to hybridize to a tumor cell may determine whether a genetic rearrangement has taken place; and a measure of Thiopurine Methyltransferase enzyme activity may reveal the presence of mutations in the TPMT gene. One skilled in the art will recognize that it is frequently more convenient and cost effective to determine the structure or activity of a protein or to measure metabolites in blood or urine than to perform an analysis directly on DNA or RNA. Such tests can be used interchangeably with tests that directly analyze DNA or DNA in the present invention. Many tests can reveal evidence indicating variations in gene sequences, expression or function including, for example, tests for proteins in serum, blood cells, tissues, assays for the expression of specific genes measured at the RNA or protein level, and assays for metabolites that are characteristic of specific gene functions or dysfunctions. It will be recognized that tests for chemical entities other than DNA or RNA may not be explicitly included in guidelines or statutes mandating informed consent. Nevertheless, the information that can be gained from such tests is often equivalent to that obtained through the analysis of DNA and RNA and presents similar benefits and risks to the individual. This invention specifically relates to tests performed on any chemical entity as a genetic test.

A "gene" is a linear sequence of nucleotides that encode or control a biological function. Genes typically direct the expression of RNA or protein which may be directly responsible for carrying out the function encoded by the gene, or the RNA or protein may be subject to modifications to carry out such functions. The gene may include, without limitation, introns, exons, promoters, or other sequences as well as chemical modifications of the nucleic acids which are involved in determining a biological function associated with that gene including the activity, amount, structure, or location of a chemical entity. Those skilled in the art will also recognize that the term gene is also used to refer to a specific series of nucleotides including characteristic variations that are associated with a clinical outcome. For example, a CFTR gene with variations that cause cystic fibrosis is often referred to as a "cystic fibrosis gene", a BRCA1 gene with variations that cause breast cancer is often referred to as a "breast cancer gene", and a phenylalanine hydroxylase gene with mutations that cause phenylketonirua is referred to as a "PKU gene."

It is recognized by the skilled artisan that the sequence of nucleotides in the gene which encode its function may vary in different individuals, and that variances or mutations within the sequences of nucleotides of the gene may change its function. The terms "mutation", "variation", "polymorphism", or "variance" refer to sequences within a gene which may differ among individuals. The term mutation is typically used to describe those variations that alter a characteristic activity of a gene or a gene product such as changes in the structure, activity, expression, availability, modification, processing, specificity, or function. Mutation more specifically describes those variations that impair activity of a gene or a gene product or are associated with an adverse clinical outcome. The terms "genetic marker", "polymorphism", or "single nucleotide polymorphism (SNP)", are typically used to refer to specific sequences within a gene that can differ among individuals that are useful as markers to identify specific genes. Use of these terms implies that the specific variation in sequence does not alter the function of the gene, however, such sequences could be associated with characteristic activity of the gene or gene product or a specific clinical outcome. When a genetic variation is associated with a specific clinical outcome, the variation, and the gene that contains that variation, are said to "cause" or be "linked" or "associated" with that clinical outcome. Those skilled in the art recognize that a sequence variance which has detrimental effects in one circumstance, can have no effect, or even have beneficial effects in other circumstances, that sequence variances that have biological effects can also be used as markers, and that markers may be very closely linked with specific clinical outcomes even if they are not causative. Specific embodiments of this invention relate to sequence variations that are associated with a specific clinical outcome either because the sequence variation alters the biological function of a gene in a way that causes the clinical outcome, or because the sequence variation is a marker that is linked or associated with a clinical outcome. The skilled artisan will recognize that it is often not known whether a specific variance is a mutation or a polymorphism, that the terms "variance", "variation", "mutation", "genetic marker", "polymorphism", and "SNP" each refer to differences in gene sequences, or positions in the genome where differences in the sequence are found between different individual, and that these terms are often used interchangeably in describing gene sequences that may be the object of a genetic test.

Relationships among genes are recognized based on similarities in structure and function, activities that contribute to common biological pathways, or activities contributing to a common pathological process or clinical outcome. "Gene family" means genes that share common structural or functional characteristics or activities. Some genes within a gene family may exhibit structural similarities due to comparable function (analogy) or evolution (homology) and may contain sequence identities, common motifs, or common functional elements, and may often be located in contiguous or closely linked regions of the chromosomes. It is recognized that genes within a family often carry out analogous biological functions, and that mutations in closely related genes can lead to similar clinical outcomes. "Pathway" refers to a sequential or intersecting set of biological functions. Several genes and gene products are be typically involved in pathways for complex biological function such as the synthesis of biological compounds, the construction of cellular or somatic structures, or the regulation of a process within the body. It is recognized that genes that contribute to a common pathway often work in a coordinated fashion, and that variances in any gene along the pathway could alter the characteristic structure, level, or expression of other genes as well as the end product. A disease, disorder or clinical outcome can often involve multiple genes as well as different variances in one or more than one gene. Genes are said to be "related" if they comprise a gene family or are involved in a common pathway, process, or clinical outcome.

The present invention relates to obtaining informed consent for genetic tests for one or more than one variances in one gene or in more than one gene. A preferred aspect of this invention of relates to obtaining informed consent for genetic tests for more than one gene where such genes are related members of a gene family, a pathway, process, or clinical outcome. Obtaining informed consent for such tests may require proportionally more information on the part of the practitioner and understanding on the part of the individual for the consent to be valid. In specific embodiments of this invention, the genetic tests is for two genes where such genes are related members of a gene family, a pathway, process or clinical outcome, three such genes, five such genes, more than 5 such genes, more than 10 such genes, or more than 100 such genes. In a specific embodiment of this invention the genetic test is a gene that includes two or more than two genes that may not be related, more than 10 genes, more than 100 genes, more than 1000 genes, or more than 10,000 genes.

"Disease" and "disorder" refer to recognized morbid or pathological events and are commonly catalogued in textbooks of medicine and standard classifications of disease such as the International Classification of Disease (ICD). "Clinical outcome" means any observable clinical event or observation including, for example, disease, disorder, health, morbidity, or mortality; growth, development, aging or longevity; the onset, progression, course, remission, relapse, symptoms, signs, or pathology of a disease or disorder; cognitive function, behavior, psychosis, or dementia; as well as drug response, or drug toxicity or the response to any intervention involving drugs, nutrition, lifestyle change, education, or surgery as well as the application of non-allopathic therapies such as, without limitation, traditional, herbal, or folk medicines, nutricuticals, osteopathy, or chiropractic medicine. The present invention relates preferably to genetic tests useful in the field of medicine for predicting a clinical outcome or determining the genetic risk of a clinical outcome.

The present invention is applicable to any clinical outcome known in the art for which genetic tests may identify a risk factor for that clinical outcome. A skilled artisan would recognize that the present invention is not limited to diseases that are traditionally identified as being genetic in origin but also to clinical outcomes that are "multifactorial", i.e. associated with combinations of genetic and environmental factors. This includes, for example, clinical outcomes such as heart disease, hypertension, heart failure, coronary vascular disease, cerebral vascular disease, stroke, peripheral vascular disease, arthritis, rheumatoid arthritis, Lupus Erythematosis (SLE), psoriasis, asthma, reactive airway disease, COPD, osteoarthritis, osteoporosis, hearing loss, cataracts, renal failure, nephritis, hepatic failure, hepatitis, pancreatitis, diabetes, infection, cancer, drug toxicity, drug resistance, drug dependence, neurological diseases, dementia, Alzheimer's disease, psychosis, neuroses, and metabolic diseases.

It is often important to perform genetic tests for multiple variations that may occur in one gene, or more than one gene, to determine an individual's risk of a multifactorial clinical outcome. For example, a mutation in one gene may predispose an individual to a high risk of a clinical outcome, which may be increased or decreased by variations occurring in another related gene. Many multifactorial diseases are also "polygenic", meaning that they are associated with variations in more than one gene. The process of obtaining informed consent for genetic tests related to a multifactorial or polygenic clinical outcome is particularly difficult since it requires the practitioner to instruct the individual in the action of multiple genes singularly and together as well as non-genetic or environmental factors that contribute to such a clinical outcome and how such non-genetic or environmental factors may be modified to alter the course or incidence of the clinical outcome. It is recognized that genetic tests are often most useful for multifactorial clinical outcomes since the identification of genetic risk factors for a clinical outcome may enable modification of complementary non-genetic or environmental risk factors that may alter the course or incidence of that clinical outcome. In specific embodiments of this invention relate to tests for genes associated with multifactorial or polygenic clinical outcomes where such outcome is associated with one gene, two genes where such genes are related members of a gene family, a pathway, process or clinical outcome, three such genes, five such genes, more than five such genes, more than ten such genes, or more than 100 such genes. A specific embodiment of this invention is an instrument for obtaining informed consent for genetic tests one gene, two genes where such genes are related members of a gene family, a pathway, process or clinical outcome, three such genes, five such genes, more than five such genes, more than ten such genes, or more than 100 such genes. In a specific embodiment of this invention is an instrument for obtaining informed consent for a genetic test that is a gene screen for two or more than two genes that may not be related, specifically more than 10 genes, more than 100 genes, more than 1000 genes, or more than 10,000 genes.

Those skilled in the art recognize that often all of the genes and variations that are related to a clinical outcome may not yet be known. Genetic tests for variations in known genes are often useful in identifying risk factors for clinical outcomes. As the number of genes that are known within the human genome increases as a result of genomic research, and as further genomic research ascribes specific functions to these genes in health and disease and identifies variances within these genes that are associated with clinical outcomes, it will be desirable to perform additional genetic tests to further refine the assessment of risk. If DNA banking is performed when the initial sample is obtained, it is often possible to use this sample for such additional tests. A specific embodiment of this invention is an instrument for obtaining informed consent for a genetic test for more than one gene, related genes, a clinical outcome, or a gene screen which authorizes DNA banking and additional genetic tests for related genes at a future time. In specific embodiments, informed consent is obtained for such tests with notification or assent of the individual.

"Genetic risk" is a quantitative and/or statistical measure of the likelihood that an individual will have a clinical outcome as a result of variations in one or more than one gene. The risk may be expressed, for example, as the fold increase in risk of a particular clinical outcome, the likelihood or probability that an individual will experience a particular clinical outcome, or an odds ratio. Various methods for determining these measures are known by those of ordinary skill in the art and are commonly described in medical journals in conjunction with the discovery of genes that are considered risk factors for specific disease and in textbooks of medicine and genetics. Risk is often described as a statistical range which describes the probability of an individual experiencing a clinical outcome, for example risks being <10%, 10-25%, 25-50%, 50-75%, 75-90% or >90%. Risk may also be determined as a fold increase in risk, for example and individual may have a a <2, 2-5, 5-10, or >10 fold increased likelihood of a clinical outcome if they have a certain genetic variation. A gene or sequence variation in a gene is a "risk factor" for a specific clinical outcome, condition and/or disease if the gene or variation is associated with a change in the risk or likelihood of that outcome.

"Genetic risk", susceptibility", "predisposition", and "risk" are often used interchangeably to describe the likelihood of a individual exhibiting a disease, disorder, or clinical outcome. It is recognized that a risk factor may refer equally to variations that increase the risk of a specific outcome or to variances that reduce the risk of that outcome. The determination of genetic risk often makes use of data from a medical and family history in addition to data describing the test result. The presence or absence of a specific variation or gene may have greater predictive value based on the family history of a specific clinical outcome and specific pattern of inheritance in that family.

The methods used to determine genetic risk as well as the statistical significance, sensitivity, specificity, and the predictive value of such information is described to the individual as part of the process of obtaining informed consent. The predictive value of a specific test may be described as the relative contribution of a specific variance or gene to a clinical outcome or to the fraction of individuals with a clinical outcome in which such outcome is attributable to a specific variance or gene. Studies suggest that the perceived accuracy of a test is particularly important to individuals who are considering whether or not to have a test performed. A description of factors including the technical specifications for the test (e.g. false positives and false negatives associated with the laboratory procedure), the statistical significance, specificity, and sensitivity of the association between a variance or gene and a clinical outcome, and the predictive value of the test result all contribute to the perceived accuracy of the test. While such information is available to those skilled in the art in reports describing the association of a specific variance or gene with a clinical outcome, it is difficult for many practitioners who are not skilled in genetics to ascertain such information and describe this information to individuals. A specific embodiment of this invention is an instrument for obtaining informed consent containing an integrated instruction element which describes the calculations for determining an individual risk based on the results of said tests, statistical processes (including the significance, sensitivity, and predictive value of the test results), personal medical history, and family history. In a specific embodiment the instrument contains stepwise instructions or a worksheet for the practitioner to determine an individual's risk.

The term "medical history" is well known in the art. The term "family history" or "family medical history" refers to information on the health of an individual's relatives, diseases they may have suffered, and the cause of death attributed to deceased family members. An individual who undergoes a genetic test is often referred to as a "proband". A family history is most commonly obtained by asking an individual about their relatives and is commonly presented as a family tree illustrating the family relationships and notes about their medical history. A family history may be obtained using computer programs such as TreeBuilder™ or Cyrillic™. Certain tests may have limited predictive value in the absence of a family history of a specific clinical outcome. Other tests may have greater predictive value if the family history is known. When genetic tests are performed for the purpose of reproductive counseling, the family history will also contain information about an individual's reproductive partner, for example a spouse, partner, or egg or sperm donor, and their related family members.

The term "family members" includes family members of the proband as well as family members of a reproductive partner. As part of the informed consent process, it is often important to collect an individual's medical history and family history to help the individual assess the potential predictive value of the test. A specific embodiment of this invention is an instrument for obtaining informed consent for one, or more than one, genetic test which includes collection of information on an individual's medical history or family history. A specific embodiment of this invention is an instrument for obtaining informed consent for one, or more than one, genetic test, containing an integrated collection element which directs the practitioner how to determine an individual's risk based on the individual medical history, family history, and results of said test. In a specific embodiment the instrument contains stepwise instructions or a worksheet for the practitioner to determine an individual's risk based on the medical history or family history. A specific embodiment of this invention is a computer program for collecting an individual's medical history or family history integrated with an instrument for obtaining informed consent.

Several medical organizations such as the National Institutes of Health, the American College of Human Genetics, and others promulgate "recommendations" on the use of genetic tests that are often based on the prevalence of a clinical outcome in a specific population or demographic group or a family history of a clinical outcome. Such recommendations are often based on the predictive value of the test and it's potential effects on an individual's quality of life, the prevalence of disease in a population or demographic group and it's potential impact on health care economics (pharmacoeconomics). Such recommendations do not prohibit the use of genetic tests by an individual, though they may have a role in decisions concerning reimbursement for such tests. An important part of the process of obtaining informed consent is to instruct an individual concerning recommendations that are relevant to the test being considered and an assessment of whether the individual meets the criteria for the test and whether such recommendations are relevant to the individuals concerns. A specific embodiment of this invention is an instrument for obtaining informed consent for a genetic test or more than one genetic test which describes recommendations to concerning such tests and guides the practitioner in an assessment of the recommended course of action for the individual. A specific embodiment of this invention is an instrument that guides the practitioner to instruct individuals concerning recommendations concerning genetic testing.

An exemplary purpose for performing a genetic test on an individual is to establish an measure of an individual's risk of a specific clinical outcome using a genetic test to determine the sequence of one gene, more than one gene, related or unrelated genes, or a gene screen in the sample, the presence or absence of one, or more than one, sequence variation genetic marker, variance, variation, mutation, polymorphism, or micro satellite sequence associated with one gene or more than one genes, the presence of one, or more than one, viral sequence, viral-like sequence, or repetitive sequence, a haplotype or genotype spanning one gene, or more than one gene, related genes, the number of copies of one or more than one gene, the amount or characteristics of RNA or protein expressed from one, or more than one, gene, the biological function of one, or more than one, gene, the arrangement of genes within the genome, the chromosome number, or integrity of chromosomes.

This invention preferably concerns genetic tests useful in medicine that identify associations with a clinical outcome such as a health, genetic disease, multifactorial diseases, or an individual's response to therapeutic drugs. Such associations are generally established through clinical trials which collect data both on the clinical outcome and genetic variations in a sample obtained from the individual. It is often necessary to perform multiple clinical trials to achieve a consensus on the significance of a specific variation on an individual's genetic risk of a specific clinical outcome. Methods for performing such studies are known to those skilled in the art, and the results of such studies are commonly reported in publications in the medical literature and presentations at scientific meetings.

Initial reports of genetic tests may involve studies on small populations which demonstrate the statistical association of a gene or sequence variation with a clinical outcome. Such studies may suggest that a test has potential utility. These data must then be supplemented by additional studies which confirm and refine the accuracy of this observation and establish the utility of the test in quantitatively determining the genetic risk of a clinical outcome. Sometimes it is necessary to perform many studies or perform meta-analyses which combine the data from several different trials to establish that a test is useful in determining the genetic risk of a clinical outcome. Studies performed as part of the research and development of a genetic test are commonly described in reports in scientific and medical journals, presentations at scientific meetings, and, sometimes, in filings made to regulatory authorities to obtain authorization for manufacture or sale of a diagnostic product designed for use in performing a genetic test. Once a genetic test has been validated through multiple clinical studies, information about such tests will be found in textbooks of medicine, genetics or clinical pathology, in materials for medical education and continuing medical education. Once a diagnostic product is approved by the FDA or offered by a certified testing laboratory, additional information is often available from the manufacturers of a diagnostic product or laboratories that perform the test on a commercial basis. More than 500 validated tests for variations in specific genes have been described and are performed by certified laboratories. Information on tests that are commonly performed in clinical practice is available to those skilled in the art, for example through the Internet locations genetest.org and geneclinics.org, textbooks such as Scriver et al., The Molecular Basis of Inherited Disease, McGraw Hill, databases available through the internet location nhgri.nih.gov, the National Center for Biological Information (NCBI) linked to the human genome project, and through academic journals of medicine and related sciences indexed through MEDLINE. New genetic tests are being discovered at a rapid rate due to continuing progress of the human genome project and associated clinical research. Those skilled in the art recognize that it is difficult to remain current on the many reports describing basic genetic research and clinical trials on genetic tests and their application to determine the genetic risk of many different clinical outcomes. Information from such reports is important both to the practitioner who must describe the test to the individual, and to the individual who must decide whether or not to have the test performed. Moreover, it is often difficult to describe medical studies in simple language that is generally understandable by individuals. A specific embodiment of this invention is an instrument for obtaining informed consent for one genetic test or more than one genetic test with an integrated instruction element which provides the practitioner with a current summary of information from reports concerning such test or tests as well as illustrative materials which facilitate the instruction of an individual concerning such tests at an appropriate level of comprehension. In a further embodiment this information is incorporated in an information element for individuals with text and illustrative materials at a level appropriate for individuals.

The invention provides instruments and methods for obtaining informed consent comprising validated elements with information concerning the genetic test, elements for instructing an individual concerning the genetic test, elements for collection of personal medical history and family history, elements for assessing the individual's retention and comprehension of information, and elements for certification of informed consent. These methods and instruments enable practitioners and individuals to obtain a meaningful and legal informed consent.

"Informed consent" or "consent" mean the process by which individuals receive information about a genetic test, are informed of the potential benefits and risks associated with performing a genetic test, and provide legally binding permission for such a test to be performed on their provided sample. The terms informed consent or consent also mean the legally binding consent provided by an individual or a document, the "informed consent document", executed by an individual which certifies their consent for a genetic test to be performed. "Assent" means the process by which an individual indicates their acceptance of a genetic test without providing a legally binding consent. For example, minors generally are considered incapable of providing a legally binding consent, but may provide assent. Standards of medical care and some state laws require that an individual provide an informed consent for a genetic test to be performed.

The elements of a document for certifying individual's consent and guidelines for what constitute an informed consent process and legally binding informed consent document are known in the art. Informed consent for genetic testing often resembles the consents obtained for human subject research as described in the Code of Federal Regulations in sections 46.116 and 46.117. These guidelines are formally applicable only to tests that are performed for research purposes and are not formally applicable to the consents required for validated genetic tests that are performed for the purpose of determining and individuals risk of a clinical outcome. Nevertheless, many informed consents used for genetic testing retain the elements of an informed consent for research purposes, in part because many genetic tests are not yet fully validated and may be considered by some to be research even though they are performed primarily for diagnostic purposes. Also, informed consent standards for research have been retained for genetic testing because many institutions seek consent to use samples and banked DNA that are obtained for diagnostic purposes for research purposes as well. An embodiment of this invention is an instrument which provides for an informed consent for genetic in compliance with Code of Federal Regulations in sections 46.116 and 46.117. An exemplary use of such consents would be for genetic tests performed for research purposes.

Other informed consents for genetic testing resemble the legal consents used for medical procedures such as surgery. The principles underlying such consents are primarily matters of state law and legal doctrine arising from common law (judicial decisions) as it applies to decisions about medical treatment and procedures. The operable standard under this doctrine is that the practitioner must disclose information that is or would be material to the patient in making his or her decision and information that a reasonable practitioner in similar circumstances would disclose. Some states in addition to the common law standard have carved out specific rules (statutes) proscribing the process for informed consent in regard to specific tests or procedures as well as the content of the disclosures that must be made to the patient facing those procedures. In some states genetic testing is treated this exceptional way and there are specific statutes on genetic testing. The statutes in most states are silent on the issue of informed consent for genetic testing, leaving the common law standard as the one that must usually be met. In the absence of a legal standard governing informed consent for genetic testing, the burden is increasingly placed on institutions and individual practitioners to provide sufficient information and instruction and collect relevant information sufficient to make the consent valid. As described herein, this may include, for example, information about the genetics, the genetic tests that will be performed, the use of genetic results, the risks and benefits of performing a test, recommendations concerning use of the genetic test, determinations of genetic risk, the use of sample, and procedures for records and protecting privacy. The preferred embodiment of this invention is an instrument which provides for an informed consent which assures compliance with statues concerning informed consent for genetic tests. An exemplary use of such consent is to obtain consent for a test performed using a diagnostic product, preferably a diagnostic product approved by the FDA. Another exemplary use of such consent is to obtain consent for a test performed by a certified reference laboratory operating under CLIA regulations as a "home brew". A preferred embodiment of this invention is an instrument that provides for an informed consent for a genetic test that is not research.

The inadequacy of current informed consent practices has been noted in many reports in the medical literature. Major problems include the inability of many practitioners to provide sufficient information and instruction for the individual to make a truly informed decision. Another problem is the difficulty of communicating technically difficult information at a level appropriate for most individuals. Another problem is the poor retention of information and understanding of information required to provide an informed consent by individuals.

"Individual" means any person who may provide consent for a genetic test or have a genetic test performed. This includes individuals who may provide consent for genetic tests performed on their own samples, individuals with legal authority to authorize genetic testing for others, for example parents who may provide consent for genetic tests of a minor, and individuals who have tests performed as a consequence of such consent.

"Practitioner", "provider", or "health care provider" are used interchangeably and include, for example, practitioners specialized in genetics with MD, PhD or MS degrees, genetic counselors, practitioners of primary care, specialties or subspecialties including physicians, nurses, physicians assistants, pharmacists, social workers, psychologists, as well as other ancillary healthcare professionals or non-professional personnel or their designees and the medical practices, hospitals, managed care organizations, or institutions for whom they are agents. The term may also include specialists trained in alternative healthcare practices including, for example, osteopaths or chiropaths. The terms refer to any provider of health services who may legally assist an individual in procuring a genetic test. The term practitioner may also relate to automated systems established by, or at the direction of, a practitioner that may be used to obtain informed consent from an individual. In such instance the term includes computer hardware and software or Internet sites that carry out such functions. In certain instances the practitioner is a virtual embodiment of the electronic medium and the instruction element is a computer program that guides the individual through the process of informed consent in an interactive manner. In some instances the virtual provider may be represented by a program or figure with synthetic voice and voice recognition systems.

"Record" or "recording" refers to a system, document, or file containing medical data about an individual. The record may contain an individual's identity and the results of genetic tests and also information about personal and developmental history, medical history, family history, clinical laboratory data, images, findings on physical exam, and previous illnesses and therapies as well as reference or links to other records. Those skilled in the art will recognize that it is important to protect the privacy of genetic records. Genetic privacy laws in many locales mandate extensive protections for the privacy of genetic information. Methods for protecting the privacy of records are known in the art and include maintaining records in a secure environment, eliminating identifiable information that can be used to associate an individual with their record in favor of codes. Patient numbers and passwords are exemplary codes. A specific embodiment of this invention is an instrument for obtaining informed consent for a genetic test or one or more genetic tests which incorporates procedures for creating a record containing genetic information and for protecting the privacy of said record. Those skilled in the art recognize that individuals need to be informed about policies and procedures used to maintain a record containing the results of a genetic test and any other medical information or identifiable information as part of the process of providing informed consent for a genetic test. Individuals must be informed what steps will be taken to protect privacy, who will be authorized to access this information, and whether the information may be used for research purposes. A specific embodiment of this invention is an instrument for obtaining informed consent for a genetic test or one or more genetic tests which describes procedures with regards to a record containing genetic information and protections for individual privacy.

A "test result" or "genetic test result" means the end result of a genetic test including, for example, the sequence of one or more genes within a sample, the presence or absence of one or more genetic markers, variances, variations, mutations, polymorphisms, or micro satellite sequences, the presence of one or more viral sequences, viral-like sequence, or repetitive sequence, a haplotype or genotype spanning one or more genes, the number of copies of one or more genes, the amount or characteristics of RNA or protein expressed from one or more genes the biological function of one or more genes, the arrangement of one or more genes within the genome, the chromosome number, or integrity of chromosomes together with known associations of such findings with a specific clinical outcome. Genetic test results may also include inferences or statistical data from clinical trials which establish the association of test results with a clinical outcome to provide an assessment of genetic risk and may include a determination of genetic risk based on the genetic test, medical history, family history, and clinical data.

"Genetic counseling" or "counseling" means the process of providing information to an individual concerning a genetic test or clinical outcome associated with a genetic risk. It includes the process of providing information to an individual concerning the use of a genetic test or genetic test result. Counseling is recognized by those skilled in the art to be an essential step in providing an individual with an accurate assessment of their genetic risk and providing an individual with assistance in the use of this information in making decisions regarding healthcare, lifestyle, family planning, reproductive counseling or other activities. Counseling is generally performed by a practitioner who has specialized training in genetics or in specific diseases. Counseling generally occurs in a practitioner's office and involves one or two sessions with a practitioner. Counseling can be performed before a test is performed as part of the process of obtaining informed consent and can also be performed after obtaining the test results to aid the individual in understanding their genetic risk and making effective use of this information.

The process of genetic counseling is described in many articles and textbooks. The process commonly includes collecting a personal medical history or family history from an individual, discussing the benefits and risks of a genetic test, communicating the results of a genetic test, and explaining the medical significance of the genetic test results, elaborating on various health related choices the individual may make on the basis of the genetic test results, and discussing the consequences of genetic test results to family members, reproductive partners, or other individuals designated physician. It is generally considered important for genetic counseling to be "non-directive", meaning that information is provided to an individual without value judgments or implied direction concerning the decision to perform a genetic test and the use of the test results. This is particularly important when genetic tests can be used for reproductive decisions, particularly decisions relating to pregnancy termination. When genetic testing is performed for common diseases, counseling frequently is concerned with the various treatment options or lifestyle choices.

A critical aspect of genetic counseling is the ability to communicate complex information about a clinical outcome, genetic tests, genetic risk, and genetic test results in a way that it is known to be understandable to most individuals. Genetic information is very complex, and it is often difficult to communicate this information to individuals who commonly have little technical background or understanding of genetics. Such communications are preferably at the $8^{th}$ grade level of written comprehension. In current practice, genetic testing is initiated by healthcare practitioners. In some instances a prescription from a practitioner is required for a certified laboratory to perform a test. A specific embodiment of this invention is an instrument for obtaining informed consent for a genetic test or one or more genetic tests which also provides a mechanism by which the practitioner can prescribe a genetic test.

A major limitation of current practice is that many healthcare practitioners, particularly primary healthcare practitioners who are in the best position to use genetic tests to assess an individuals genetic risk or predisposition to diseases before they occur, are not sufficiently familiar with the current literature on genetic tests to provide individuals with information or instruction, collect adequate family histories, or obtain a meaningful and legal informed consent. Genetic counseling can be obtained through a referral to a healthcare practitioner specially trained specially in genetics. The genetics professional commonly meets with the individual one or two times, and the responsibility for ongoing medical care will continue to reside with the referring practitioner. It not practical to refer all individuals to practitioners specially trained in genomics. It is anticipated that by 2006, 10-40 million tests will be performed annually. At the present time there are <3,000 individuals with specialized training in genetics. The instruments described in this invention have utility in providing practitioners with the information and instructions required to provide counseling to individuals sufficient to obtain an informed consent.

Information about genetic risk is available from sources other than healthcare practitioners. Patient support groups specializing in certain disorders or classes of disorders are often an important source of information for individuals. General information is also available on the Internet or world wide web, for example at Internet locations such as genetests.org, geneclinics.org, nih.gov, rarediseases.org, genetichealth.com, dna.com and genesage. While many individuals seek information from such sources, the quality and relevance of the information varies widely and this information is not integrated with the counseling provided by the practitioner or the informed consent process.

Samples are generally obtained by the health care practitioner, a central blood drawing service of a hospital or health care clinic, or a satellite facility of a diagnostic testing service. Samples can also be obtained by an individual, for example by using an OraSure device. Samples are commonly sent to genetic testing services, often referred to as reference laboratories for genetic tests, such as Genzyme Genetics, Quest Diagnostics, LabCorp, or Specialty Laboratories, certain clinical laboratories or hospital based, or academic research laboratories. Such laboratories are commonly regulated by Clinical Laboratory Improvement Act (CLIA) which sets standards for the performance and reporting of test results. Genetic tests are not currently regulated by the FDA though, in the future, may be developed as FDA approved diagnostic tests or kits for use by diagnostic laboratories or even home use. Genetic tests available from a certified reference laboratory or available as diagnostic kits are generally referred to as validated, meaning they have been subject to clinical evaluations and have demonstrated clinical utility. Such tests are differentiated from those that are not yet validated and are performed on a research basis. A preferred embodiment of this invention relates to validated tests that are not covered by guidelines governing clinical research. A separate embodiment of this invention relates to tests that are designed as research where the guidelines for informed consent must comply with sections 46.116 and 46.117.

"Validated" is known in the art and refers to the process by which a method or an instrument is established in a reproducible fashion and subjected to testing to establish its utility and validity. For example, a clinical procedure or laboratory test is validated if it is performed in a reproducible manner and is shown through research to have clinical value. Methods or instruments are validated through an iterative process of developing the text and materials that comprise the instrument, and then testing these texts or materials in a clinical study to determine whether they are understandable. Texts or materials which are poorly understood by study subjects are then revised and retested until a desired level of comprehension is achieved in the study population. Larger studies can then be performed to demonstrate the efficacy of the entire instrument in achieving a desired level of retention and comprehension in a borad population representing different ethnic, demographic, or socioeconomic groups. Methods for validating an instrument are known in the art and involve testing the instrument on a sufficiently large number of people to perform a statistical analysis on the data. A set of performance specifications are establish concerning the retention and understanding of information concerning the genetic test by the individual, the proper handling of the sample and genetic information, and the satisfaction of both the individual and the practitioner in the adequacy of the process. Statistical analysis is performed to demonstrate that the instrument adequately meets the performance specifications. In a specific embodiment, the instruments described in this invention are validated through clinical studies that demonstrate their utility in providing information and counseling to individuals and obtaining a valid informed consent. Use of a validated instrument often involves training in the use of the instrument quality controls designed to maintain consistency in the use of the method or instrument, as well as quality assessment and process improvements designed to maintain the quality of the method or instrument, and work towards improvements in efficacy or efficiency.

"Training" means curriculum and materials for instructing practitioners in the use of the instruments and methods described herein. This may involve specialized materials for use in medical education, continuing medical education, or group or individualized instruction of practitioners in the use of the instrument by those skilled in the use of these instruments.

"Quality control" and "quality assessment" refer to the ongoing process of measuring whether performance specifications are being achieved through use of the instrument. Quality control is achieved by integrating elements into the instrument that assess whether the performance specifications are met and by implementing procedures for review of these elements on an ongoing basis. Such review may involve analyzing a random sample of results, results in selected regions or populations based on the particular test being performed, the specialty of the practitioner, or the health, language, ethnic origin, or socioeconomic status of the individual.

Validated instruments are known in the art, for example, for neurocognitive testing. For examples tests such as the Wechsler Individual Achievement Test (WIAT), Wechsler Adult Intelligence Scale (WAIS), Boehm Test of Basic Concepts, California Verbal Learning (CVLY-II), Kaplan Baycrest Neurocognitive Assessment, Wechsler Adult Intelligence Scale (WAIS-III), Wechsler Intelligence Scale for Children (WISC-III), Bayley Scales of Infant Development (II) and many other tests have been developed to test individuals for neurological, developmental, and psychological performance and achievement. Once developed these tests are subjected to clinical evaluation to validate the reliability of the instrument. Practitioners who administer these tests do so by purchasing packages with the exam that are provided to the individual taking the test, an instruction set that provides stepwise guidance on performing the test, and a scoring sheet to score the individuals answers and compute established performance parameters. Other validated instruments are used to assess clinical depression such as the Beck Depression Inventory (BDI), Depression Scale (DEPS), Duke Anxiety Depression Scale (DADS), Hopkins System Checklist (HSCL), Primary Care Evaluation of Mental Disorders (PHQ), and the Symptom Driven Diagnostic System-Primary Care (SDDS-PC).

"Integrated" means elements that are linked in their content, components, structure, sale, operation, or use. An instrument is integrated if it comprises two or more than two integrated elements. Elements are integrated if there is cross-reference between the elements, coordinated text or illustrative materials between the elements, or explicitly complementary functions in the design, content, composition, materials, function, or intended use of the elements. An example is an instruction element that guides the practitioner through the process of providing information in an information element to an individual, collecting a medical history or a family history using a collection element, assessing the individual's retention and comprehension of the information using an assessment element and certifying their consent using a certification element. Other examples of integration include providing the practitioner with text or illustrative materials in an instruction element that match or complement the information provided directly to the individual in an information element, providing the practitioner with instructions, in an instruction element, for assessing, using an assessment element, an individual's retention and understanding of the information in the information element, and providing the practitioner with materials for obtaining and labeling a sample or sample collection device, creating a genetic record, or billing along with instruction in the use of such materials.

A checklist is a useful component of an integrated instrument. "Checklist" means a form in printed or electronic medium that lists key steps involved in obtaining an informed consent using the instrument which is designed such that the practitioner can confirm when each step has been performed and/or completed. The checklist can be used by the practitioner in practicing the method of obtaining informed consent using the instrument, can be incorporated in a medical record to document the method that was used, and can be used for quality control of the method and instrument. For example, the checklist may list contain entries related to the description of the genes involved in a clinical outcome, the genetic test, the nature of a specific clinical outcome, the role of genetic tests and test results in managing a clinical outcome, how genetic tests are performed, the nature and purpose of informed consent, how samples are obtained and handled, what happens to the sample after the test is performed, whether the sample can be used for other purposes, whether the sample will be available for additional tests in the future, who will perform the test, who receives the test results, what information will be placed in a medical or genetic record, how this information may be used, policies for protecting the privacy, as well as other information included in the information element or instruction element. A specific embodiment of the method is use of a checklist for obtaining informed consent using an integrated instrument.

Worksheets are also useful components of an integrated instrument. "Worksheet" means a form in printed or electronic medium which is used for the collection or processing of data. Worksheets are typically designed to prompt the user to collect and record certain data, for example by filling in the blanks on the form or providing answers to specific questions. Worksheets can also guide the user through a series of calculations by arranging data entries in a convenient layout, providing additional data or data tables necessary for the calculation, and indicating the mathematical functions to be used. Worksheets are recognized to be useful in obtaining a medical history, review of systems, and family history by providing a list of specific symptoms, signs, diseases, or clinical outcomes that should be addressed. Worksheets can be used to calculate genetic risk based on a family history or a genetic test result by providing a format for systematizing the data, the calculations that need to be performed, and statistical tables.

The invention provides for the integration of elements for obtaining informed consent including two, or more than two, or the following: an information element, with information for individuals concerning genetic tests, an instruction element for practitioners to assist in providing information to the individual, obtaining an informed consent, obtaining a sample, and establishing a record, a collection instrument for obtaining an individuals medical history and family medical history, an assessment element to assess the individual's retention and comprehension of information, a certification element for certifying an individual informed consent, as well as elements for obtaining and labeling the sample, creating a genetic record, and billing. A specific embodiment of this invention is the integration of the elements required to obtain a valid informed consent into an instrument that may be used by a practitioner to obtain informed consent from an individual.

Integration is achieved by development of elements designed to be used in a coordinated fashion. For example, it may first be determined by experts what information an individual should receive and what information they should retain and understand in order to provide a valid informed consent. An information element for the individual may then be developed along with an element for assessment that would ascertain whether an individual retained and understood this information. An instruction element may then be developed as a teaching guide for the practitioner through the process of obtaining consent. These elements may then be subjected to validation to determine whether use of the instruction element and information element, in fact, provides most individuals with the requisite information to provide consent. Several iterations may be required in the development of these integrated elements to achieve the performance specifications. Integration is also achieved by providing the practitioner with all of the elements required to complete the process of achieving informed consent, create a medical record, and processing a genetic test. Integration may also be achieved by providing different elements required to obtain informed consent and process a sample together, for example in the form of a booklet or package that contains several elements. Integration may also be achieved in the design of the elements such that entries made in one element are systematically incorporated in another element, for example through the use of carbon copies. Such integration has utility both in improving the efficiency and quality of the informed consent process.

"Electronic medium" are known in the art and the term refers, without limitation, to software and hardware capable of carrying out the unique methods and embodiments described herein including the computer code, concept, content, components, design, construction, appearance, look, feel, animation, text, graphics, organization, storage systems, presentation systems, and function of the medium. In an embodiment of this invention, the electronic medium are interactive such that the individual or the practitioner may direct or query the system. In an embodiment of the present invention, such electronic medium contains synthetic speech and speech recognition capabilities.

The terms "printed medium" or "printed materials" are generally known in the art and refer, without limitation, to text or illustrative materials on paper in bound or unbound form, boards, labels, transparencies, photographs, or objects as well as the concept, content, components, design, construction, appearance, look, feel, figures, graphics, and organization of the materials. In a preferred embodiment of this invention the instrument comprises elements in printed medium that can be separated.

"Carbon copy" refers to the imprinting of entries made by a practitioner or individual on multiple pages of the instrument simultaneously, for example through the use of carbon paper or other paper or materials designed for that purpose. Carbon copy also refers to the copying of information entered into one element through electronic means to other integrated elements within the instrument, for example by copying into another element in electronic medium or through the printing into a printed medium. In a preferred embodiment of this invention, the printed materials are constructed such that a carbon copy of information entries in one element are copied on other integrated elements.

"Text" is known in the art and means written materials whether in printed or electronic form including associated images, diagrams, or pictures. "Illustrative materials" means materials designed to assist the instruction of the individual and promote understanding and retention of the information. Illustrative materials may include, without limitation, diagrams, pictures, photographs, poster, displays, exercises, models, objects, games, props, or worksheets. Illustrative materials may be in the form of printed medium or electronic medium and may include various objects. For example, diagrams showing different patterns of inheritance may aid the understanding of the role of inheritance of a particular gene or the inheritance of clinical outcome. Photographs or models may aid the understanding of a clinical outcome. Exercises, games, or worksheets may aid the comprehension and retention of information. An "object" may be used to illustrate principles of genetics, for example the use of dice to illustrate principles of chance and probability.

This invention comprises printed materials with text and illustrative materials for carrying out the unique methods and embodiments described herein. Preferably, the invention is in the form of a booklet with printed materials comprising each of the elements bound in such a way that the elements are integrated. For example, a checklist within the instruction element can be used by the practitioner and then incorporated in the recording element, answers to questions in the assessment element or the certification on the certification element can be marked by the individual and incorporated in the recording element, and information in the labeling element and billing element can be incorporated in the recording element. Preferably this is achieved through the design of the instrument such that a carbon copy of entries in one or more elements is also made in the recording element when the initial entry is made in the other elements of the booklet. Preferably also the invention is in the form of a booklet with printed materials comprising two or more elements bound in such a way that the elements can be separated. For example, the information element may be separated and provided to the individual, various illustrative materials may be separated for use in instruction of the individual, the recording element can be separated for incorporation in an individual's general medical record, the label element may be separated and affixed to a sample collection device, and the billing element may be separated for processing by a billing office. This is achieved through the design of the instrument using methods known in the art such that pages are bound together with certain pages perforated so as to enable easy separation of selected pages from the other pages of the instrument, or certain pages are affixed by adhesives which provide for clean separation of one or more pages from the instrument. For example, the information element may comprise a booklet that can be provided to the individual and retained for their information. For example, elements for assessment, certification, records, labeling, and billing, may comprise separate pages that can be separated from the instrument, and illustrative materials may be separated for display on a board. In one embodiment, the pages or printing of different elements within the instrument are color coded for efficient separation. In alternative embodiment, the different elements are distinguished by size of the page for efficient separation. The instrument may be a kit containing different printed materials including text, illustrative materials or objects in a single package that can be separated for use by the individual and practitioner.

Alternatively, this invention comprises electronic medium capable of carrying out the unique methods and embodiments described herein. This is achieved through the design and development of computer programs wherein the different elements are presented to the individual or practitioner as different pages on a computer screen, windows, or pages printed by the computer program. Preferably, the elements are integrated through the use of a menu or, more preferably, links between the elements. The elements are also preferably linked by the copying of information entered into one element into one or more integrated elements. For example, the information element may be linked to the assessment element so that the individual can answer questions about the information which is provided and return to review the information if necessary. The instrument may be accessible via the Internet or loaded on a specific computer. Methods are well known to those in the art for constructing such functioning systems using HTML or JAVA.

The instrument may contain elements comprising printed materials and elements comprising electronic medium. For example, the information element may be an audio tape, video tape or interactive computer system, while the elements for certification, labeling, or records are printed materials. Alternatively, the information element may be a pamphlet, while other elements of the instrument are in electronic medium. Preferably, the electronic medium is designed such that certain elements can be printed from the program. For example, the information element may be printed for the individual's records and the recording element, labeling element, or billing element can be printed for use by the practitioner.

The elements of the invention may be in any language, for example, English, Spanish, French, German, Italian, Russian, Japanese, Chinese, or Hebrew. Preferred are elements which use the primary language of the individual. When the primary language of the individual is different than the primary language of the practitioner, certain elements may be in the language of the individual and other elements in the language of the practitioner. For example, the information element, collection element, assessment element, and certification element may be in the primary language of the individual, while the instruction element, assessment element, recording element, billing element are in the primary language of the practitioner. In further embodiments, the instrument integrates translations for the practitioner of elements that are in the primary language of the individual within the element. One or more of the elements of the instrument or components thereof may be in Braille or in oral form (e.g. audiotape, videotape, or electronic systems with synthetic or recorded voices) for those who are visually impaired or otherwise unable to read printed materials.

B. Detailed Description of the Elements

This invention describes integrated instruments and methods with utility in obtaining informed consent for genetic tests. The instruments described in this invention comprise the following integrated elements:
(a) an information element for an individual concerning a genetic test for one gene, more than one gene, related genes, a clinical outcome or a gene screen;
(b) an instruction element for the practitioner useful in providing instruction to the individual and guidance in the use of the instrument and obtaining informed consent; and
(c) a certification element, which can be used to certify the individual's consent for the test.

The instrument of the invention may optionally include any one or more than one of the following additional elements:
a collection instrument for collection of information concerning the individual's personal medical history or their family medical history;
an assessment element for assessment of the individuals retention or comprehension of the information;
a labeling element for labeling a sample or sample collection devise or diagnostic used for genetic testing with the identity of the individual;
a billing element for payment by the individual or through a reimbursement agency
a recording element that can constitute or be incorporated in an individual's medical record;
a training element for training the instructor in the use of the instrument;
a quality control element for monitoring performance of the practitioner and the performance of the instrument; and
an indemnification element that can constitute an agreement to indemnify the practitioner.

In a preferred embodiment the instrument comprises in an integrated manner the information, instruction, certification and assessment elements. In an alternative preferred embodiment the instrument comprises in an integrated manner the information, instruction, certification and collection elements. In another preferred embodiment, the instrument comprises in an integrated manner the information, instruction, certification, collection and assessment elements. In yet another preferred embodiment, the instrument comprises in an integrated manner the information, instruction, certification, collection and assessment elements and at least one of the elements selected from the group consisting of a labeling element, a billing element, a recording element, training element, a quality control element, and an indemnification element. Alternatively, the instruments described in this invention comprises the information, instruction and certification elements and two, or more than two, or the following: a collection element, an assessment element, a labeling element, a billing element, a recording element, a training element, a quality control element, and an indemnification element. More specifically, the instruments described in this invention may comprise the information, instruction and certification elements and two, three, four, five, six, seven, or eight of the other elements described herein.

The elements comprising the invention may be integrated individually in a pair wise manner or in groups within the instrument, or, in alternative embodiments of the invention, the instruments may be comprised selectively of such integrated elements. For example, the information element may be integrated with one or more of the following elements: an instruction element, a collection element, an assessment element, a certification element, a labeling element, a billing element, a recording element, and a training element. Specifically, the information element may be integrated with the instruction element, a certification element, or an assessment element or all three of said elements. Alternatively, the information element may be integrated with the instruction element, a certification element, or a training element or all three of said elements.

In another example, the instruction element may be integrated with one or more than one of the following elements: an information element, a collection element, an assessment element, a certification element, a labeling element, a billing element, a recording element, and a training element. Specifically, the instruction element may be integrated with a certification or assessment elements. The information and instruction elements may be integrated with one or more than one of the following elements: an assessment element, a collection element, a certification element, a labeling element, a billing element, a recording element, and a training element. Alternatively, the instruction element may be integrated with an assessment element and one or more than one of the following elements: an information element, a collection element, a certification element, a labeling element, a billing element, a recording element, and a training element. Alternatively, the instruction element may be integrated with a certification element and one or more than one of the following elements: an information element, a collection element, an assessment element, a labeling element, a billing element, a recording element, or a training element. Specifically, the instrument may contain an instruction element integrated with a training element. Alternatively, the instrument may contain an instruction element integrated with a training element and one or more than one of the following elements: an information element, a collection element, a certification element, an assessment element, a labeling element, a billing element, or a recording element. Specifically, the instrument may contain an instruction element integrated with information and assessment elements. Alternatively, the instrument may contain an instruction element integrated with information, assessment, and certification elements. Alternatively, the instrument may contain an instruction element integrated with certification and training elements.

In another example, the instrument may contain a certification element integrated with one or more than one of the following elements: an information element, an instruction element, a collection element, an assessment element, a labeling element, a billing element, a recording element, or a training element. Specifically, the instrument may contain a certification element integrated with an assessment element. Alternatively, the instrument may contain a certification element integrated with an assessment element and one or more than one of the following elements: an instruction element, an information element, a collection element, a certification element, a labeling element, a billing element, a recording element, and a training element. Specifically, the certification element may be integrated with a recording element. Alternatively, the certification element and recording element may be integrated with one or more of the following elements: an information element, an instruction element, a collection element, a labeling element, a billing element, and a training element.

In another example, the instrument may contain a training element integrated with one or more of the following elements; an information element, an instruction element, a collection element, an assessment element, a certification element, a labeling element, a billing element, and a recording element. Specifically, the instrument may contain a training element integrated with an instruction element.

The instrument may be used to obtain informed consent for a genetic test for one gene. Alternatively, the instrument may be used to obtain informed consent for a genetic test for more than one gene, related genes or for genes associated with a clinical outcome. The instrument may also be used to obtain informed consent for a gene screen test.

The information element comprises text and illustrative materials intended to provide an individual with sufficient knowledge about a genetic test, the potential medical consequences of a genetic test, and the procedures involved in genetic testing to provide a meaningful and legal informed consent. The information element is integrated with one or more other elements of the instrument. The type of information required for an individual to provide a valid informed consent is known in the art and disclosed in various textbooks and publications in scientific journals as well as in courses and presentations by individuals recognized to be opinion leaders in the field. The information element provides such information in the form of text and illustrative materials. The text and illustrative materials include information about a specific clinical outcome, the genes that constitute risk factors for that clinical outcome, the significance of different genes that constitute risk factors for that clinical outcome, the potential actions that could be taken to prevent or treat the clinical outcome based on genetic test results, how genetic tests are performed, the purpose of informed consent, the process of obtaining informed consent, how samples are obtained and handled, the significance and process of DNA banking, what happens to the sample after the test is performed, what happens to banked DNA, whether the sample can be used for other purposes, whether the same will be available for additional tests in the future, who will perform the test, who will receive the test results, what information will be placed in a medical or genetic record, how this information may be used, policies for protecting the privacy and confidentiality of test results, the availability, nature and role of genetic counseling, factors which should be considered in deciding whether to have a genetic test including the benefits and risks of a genetic test, potential uses of test results in health and wellness management and lifestyle decisions, the recommendation of professional organizations. The information element may also describe in the form of text and illustrative materials the liabilities of various parties that may be involved in providing information, handling the sample, performing the test results, or providing the individual with guidance on the use of the test results. The information element may also have background information about genetics to aid understanding of genetic testing in general, references (for example, books, publications, web sites) to more detailed information, and contacts (for example, the names, telephone numbers or web addresses of organizations or individuals) who the individual can contact if they wish further information. In a specific preferred embodiment, the information element is validated.

The text and illustrative materials are designed for individuals with an $8^{th}$ grade education or level of reading comprehension. Methods for assessing the grade level of language used in such an element are known in the art. Optionally, the integrated instrument may contain information elements at different grade levels or links or references to advanced information for individuals who have the interest and ability to comprehend such information and the practitioner will select an information element with an appropriate level of complexity for the individual. For example, text and illustrative materials may be provided for individuals at the $8^{th}$ grade level, $12^{th}$ grade level, college students, college graduates, or postgraduate level. Information can be provided in any language, preferably the primary language of the individual. Alternatively, information can be provided orally by an audiotape, videotape, or computer for individuals who may be illiterate.

In a specific embodiment, the text and illustrative materials comprise printed material. Preferably the text and illustrative materials can be physically separated from the other elements and provided to the individual for their review or study. In an alternative embodiment, text and illustrative materials comprise electronic medium. In an embodiment, the instruction element may be a video that provides information to the individual or an audiotape linked to illustrative materials. In a specific embodiment, the text and illustrative materials are on the Internet or computer. In another alternative embodiment, the text and illustrative materials are comprised of a combination of printed materials, electronic medium, and/or objects.

The instruction element comprises text and illustrative materials intended to assist a practitioner in the use of the elements that comprise the instrument. The text and instructional materials contain instructions for the practitioner on use of the instrument, instructions for to be provided by the practitioner to the individual on the use of the instrument and the process of providing informed consent, instructional materials to guide discussion with the individual concerning a genetic test for one gene, more than one gene, related genes, a clinical outcome, or a gene screen, the nature of a specific clinical outcome, and how to prevent or manage a clinical outcome including the role of genetic tests and test results, the genes that constitute risk factors for that clinical outcome, the significance of different genes that constitute risk factors for that clinical outcome, the potential actions that could be taken to prevent or treat the clinical outcome based on genetic test results. The text and illustrative materials also contain to instructional materials to guide a discussion with the individual concerning how genetic tests are performed, including the nature and purpose of informed consent, how samples are obtained and handled, what happens to the sample after the test is performed, whether the sample can be used for other purposes, whether the sample will be available for additional tests in the future, who will perform the test, who receives the test results, what information will be placed in a medical or genetic record, how this information may be used, policies for protecting the privacy and confidentiality of test results, the availability, nature and role of genetic counseling, instruction guiding the individual's choice whether or not to perform a test, potential uses of test results in health and wellness management and lifestyle decisions, the recommendation of professional organizations. instructions for using the element for assessment including answers to the questions and instructions to determine whether the individual demonstrates a minimum adequate level of understanding, instructions for completing informed consent, instructions for obtaining sample, instructions for labeling sample, instructions for completing medical record, additional background information on patterns of inheritance, genes, DNA, chromosomes, specific clinical outcomes, psychosocial issues in genetic testing, the potential for genetic discrimination, and answers to frequently asked questions. The text and illustrative materials in the instruction element are integrated with those in the information element in that the text and illustrative materials in each element may be "overlapping", i.e., one or more portions of the text and/or illustrative materials in the instruction element may be quoted in, recapitulated in, or similar in wording or meaning, to a corresponding text and/or illustrative material in the information element. The instruction element is intended for use by the practitioner in helping individuals understand and retain the information in the information element. The instruction element can be in any language, most preferably the primary language of the practitioner.

The instruction elements also direct the practitioner in how to, inter alia, (a) provide information to an individual concerning one or more than one genetic tests; (b) collect information concerning the individual's personal medical history or their family medical history; (c) perform an assessment the individual's retention or comprehension of said information; (d) obtain certification of the individual's consent for said test; (e) obtain a sample for testing; (f) properly label the sample; (g) deliver the sample to the appropriate laboratory for the test to be performed; (h) bill the individual either directly or through a reimbursement agency and (i) add appropriate information to the individual's medical record. Preferred embodiments provide the instructions in a stepwise manner.

In a preferred embodiment, the instruction element contains a checklist, and in an embodiment of the method, the practitioner uses a checklist to document the steps in obtaining the informed consent. In a preferred embodiment the instruction element contains specific language designed to ensure standardization and quality of the informed consent to be used by the practitioner to instruct the individual. The checklist contains items to be discussed with the individual and contains the steps that comprise the method for use of the instrument. In a preferred embodiment of the method, the practitioner uses the checklist and integrated elements in obtaining informed consent. In a specific embodiment, the instruction element is validated.

The text or illustrative materials comprising the instruction element describe the test to be performed, the potential test results, the medical significance of potential test results as well as choices that an individual may be able to make based on the test results. The instruction element may also provide general background information about genetics to aid understanding of genetic testing by the individual. The instruction element may describe specific benefits and risks of performing the tests and recommendations concerning such the use of such tests. The text and/or illustrative materials may describe the procedure for obtaining a sample and performing a test, the disposition and potential future use of the sample as well as the test results, guidelines for protecting the privacy and confidentiality of the individual, procedures for banking DNA, restriction on the use of banked DNA, as well as legal boundaries concerning the liability of various parties that may be involved in providing information, handling the sample, performing the test results, or providing the individual with guidance on the use of the test results. The text and/or illustrative materials comprising the instruction element may also provide stepwise direction on how to collect a personal medical history or a family medical history, preferably using an integrated collection element. In a preferred embodiment, the instruction element includes text, methodology and illustrative materials that teach the practitioner how to use the information collected in the collection element. More preferably the instruction element comprises a worksheet that enables the practitioner to assess the significance of the personal medical history or family medical history, for example, by calculating the risk of a specific genetic disorder based on the number of affected family members. In a preferred embodiment, the instruction element includes text for calculating genetic risks based on the family history. In a further embodiment, the instruction element may comprise a worksheet or computer program that enables a calculation of genetic risk based on family history.

In a preferred embodiment in which an assessment element is included in the instrument, the instruction element directs the practitioner through an assessment of the individual retention or comprehension. In such embodiments, the assessment element contains text comprising a series of questions to be asked by the practitioner in assessing the individual's retention or comprehension of the information and a corresponding answer set. In an alternative embodiment, the element for assessment comprises a series of questions in the form of a questionnaire that can be completed by the individual, and the instruction element directs the practitioner in how to administer the questionnaire and provides correct answers to these questions as well as guidelines for responding to correct and incorrect answers.

In a specific embodiment of the present invention, the instruction element is printed material. In a preferred embodiment the instruction element can be physically separated from the other elements of the instrument and retained for use by the practitioner. In an alternative embodiment the information element is one element of an instrument comprising printed materials and electronic medium. For example, the instruction element may be printed material with directions on the use of a computer program or web site that comprises the information element or other elements of the instrument. In further embodiments the information element is comprised, without limitation, of mixed medium including printed materials, electronic medium, and objects.

In an alternative embodiment, the information element comprises text and illustrative materials in electronic medium. In a specific embodiment the instruction element is in electronic medium comprised of text and illustrative materials that are used by the practitioner to instruct the patient regarding the genetic test and the use of the instrument. In a specific embodiment the practitioner is a virtual embodiment of the electronic medium and the instruction element is a computer program that guides the individual directly through the process of informed consent in a stepwise or interactive manner. For example, the instruction element may be a computer program to present the individual with information using the information element, perform an assessment of the individual's retention and understanding using the assessment element, create the record using the recording element, provide a label for the sample using the labeling element, and arrange payment using the billing element. The instruction element in electronic medium may also provide the individual with direction on the appropriate use of one or more of the elements, monitor the progress of the individual through the informed consent process, and provide additional information or directions as necessary to assist in the effective completion of the informed consent process and proper processing of the sample. In an embodiment, the instruction element may be a computer program that instructs the individual in the use of the instrument. In a specific embodiment, the computer program may integrate the information element and the instruction element. In an embodiment, the instruction element in electronic medium may use an animated figure, photographic or video image and/or a synthetic voice to represent a practitioner in presenting information to the individual and/or instructions on the use of the instrument. In a specific embodiment the electronic medium employs synthetic voice and voice recognition systems.

The instruction element may contain objects that can be used by the practitioner in presenting information to the individual. Objects may include models, diagrams, or pictures of the human body or disease states, for example, representations of the skeleton, organs or tissues, "Games of chance" such as dice may be useful in explaining the statistical nature of genetic risk and may be incorporated as objects within the instruction element. These objects may be integrated with the information element with text or illustrative materials designed to demonstrate genetic principles.

The certification element is a document that can be signed by an individual to signify their consent for a genetic test to be performed. This document resembles informed consent documents known in the art and, by itself, is designed to comply with any legal or statutory requirements for certification of informed consent. The informed consent document comprising the certification element summarizes the individual's understanding of the specific test that will be performed, the benefits and risks involved, the procedure for obtaining a sample and performing the test, the disposition and potential future use of the sample and the test results, guidelines for protecting the privacy and confidentiality of the individual and their genetic information, and information concerning the liability of parties involved in providing information, handling the sample, performing the test, or providing the individual with guidance on the use of the test results. The certification element may also enable the individual to signify their consent for DNA banking as well as stated uses of the banked DNA. The certification element may also include the individual's consent to specific forms of follow up, may indicate who should receive the test results and how they want the results to be reported, may indicate whether they are interested in receiving information with updates on research about the genetic test, the test results, or new tests related to a clinical outcome. The document contains blank signature lines for execution by the individual, the practitioner, and at least one witness. The certification element is integrated with other elements of the instrument. In preferred embodiments, the certification element is integrated with the information element and instruction element. For example, the certification element may recapitulate essential information from the information element or may incorporate the summary of instruction provided to the individual or a checklist from the instruction element. In another preferred embodiment, the certification element is integrated with the recording element. In further embodiments, the certification element may be integrated with the assessment element, for example by incorporating the results of the assessment. In a specific embodiment, the certification element is validated.

The certification element comprises printed material that preferably includes multiple execution copies or carbon copies so that duplicate copes can be retained by the individual and incorporated into the medical record, or provided to others who may require certification of the individual's consent. In an alternative embodiment, the certification element is in electronic form and execution is by a legally recognized electronic signature. In a preferred embodiment, the instrument is constructed such that the signature entered into the certification element is directly entered into other elements, for example the recording element or the labeling element. The certification element may additionally include a prescription to be issued by the practitioner, which authorizes a testing laboratory to perform a test. Such prescriptions for tests are required by certified laboratories in certain states. In a preferred embodiment, certification element is integrated with the labeling element such that the prescription entered into the certification is copied on the label provided to the laboratory with the sample.

The collection element comprises text and/or illustrative materials useful in obtaining an individual's personal medical history or their family medical history. Methods for obtaining personal medical history are described in basic textbooks and clinical manuals, and tools such as worksheets and computer programs are well known in the art. Such texts and illustrative materials contain questions about past illnesses as well as a "review of systems" with questions concerning the health of various bodily functions. Standardized instruments and methods for obtaining a family medical history are also known in the art and involve the cataloguing of information concerning the individual's family members, determining their familial relationship to the proband, and recording their state of health or cause of death. This information is typically portrayed in the form of a family tree. Methods for recording an individual's medical history and family history are known in the art and may comprise printed materials with worksheets or may comprise electronic medium in the form of computer programs such as GeneTree of Cyrillic. In the preferred embodiment, the collection element is integrated with other elements of the instrument. For example, the collection element may be integrated with the information element such that the individual is provided with information about the genetics of different diseases, disorders, or clinical outcomes that would be useful in a personal or family history. The collection element may be integrated with the instruction element such that the practitioner can instruct the individual in the use of the element and use the data to perform a quantitative assessment of genetic risk. In a specific embodiment, the collection element is validated.

In a further embodiment the collection element may be linked to the recording element to enable follow-up of the proband and family members with information regarding the genetic test or test results that may be relevant to clinical outcomes of the proband or family members. For example, the collection element may incorporate email, telephone, or mailing addresses of family members or provide the proband with materials that can be mailed to these individuals. Information from these family members may be incorporated in the collection element to provide a more complete and accurate collection of the proband's medical and family history. In a specific embodiment, the collection element is integrated with the certification element to assure proper authorization of procedures to contact family members. In a specific environment, the collection element may be integrated with the certification element and recording element, enabling the proband and family members to authorize the distribution of genetic and medical information, receive-follow-up, and release genetic information to their respective medical records The assessment element comprises a series of questions in the form of text and illustrative materials that are posed to the individual to assess their retention and comprehension of information. The legal principle underlying informed consent for genetic testing is that an individual must have sufficient comprehension of information to make an informed choice. The assessment element is designed to determine whether the individual has retained and comprehends sufficient information concerning the genetic test to provide such a valid informed consent. The assessment element includes text comprising basic questions covering information presented in the information element and instruction element concerning a genetic test for one gene, more than one gene, related genes, a clinical outcome or a gene screen to be performed, possible test results, DNA banking, the medical significance of potential test results, standard of care recommendations concerning such tests, the choices available based on the test results, the specific benefits and risks of performing the tests, the procedure for obtaining a sample and performing a test, the disposition and potential future use of the sample as well as the test results, guidelines for protecting the privacy and confidentiality of the individual, and legal issues regarding liability. The text of the assessment element may incorporate questions in the form of short answers, multiple choice, true/false, matching, fill in the blank, or other test formats known in the art. The assessment element is integrated with other elements of the instrument. In a specific embodiment, the assessment element is validated.

In a preferred embodiment, the assessment element comprises printed material in the form of a questionnaire that can be completed by the individual. In an alternative embodiment, the assessment element is in the form of interactive electronic medium in which the individual reads and responds to questions on a computer or the Internet. In another alternative embodiment, the assessment element is integrated with the instruction element and the practitioner reads the questions to the individual and the individual either provides answers on a worksheet or responds orally and the practitioner records the answers. In a specific embodiment, the assessment element is integrated with the information element with provides the individual with sufficient information to correctly answer questions in the assessment, is integrated with the instruction element which provides the practitioner with directions on administering the assessment and scoring the results, is integrated with the certification element such that certification can only be provided if the individual exhibits a minimum number of correct answers on the assessment, and integrated with the recording element which incorporates the individual's responses to the questions and/or the score on the assessment.

The labeling element comprises materials that are to be attached to a sample or a sample collection device to identify the individual, direct the sample to the appropriate laboratory, and designate how the sample is extracted and banked, and what test is performed. The labeling element may also designate, either in text, color code, or other recognized medium, whether the sample is to be preserved, whether DNA is to be banked, and what uses may be made of the sample. In preferred embodiments, the element comprises one or more than one copy of printed materials that form a label that is affixed to the sample or one or more sample collection devices used in the course of obtaining a sample, handling the sample, banking DNA, and performing the genetic test. In a specific embodiment, the labeling element comprises printed materials with an adhesive backing that can be separated from the instrument and attached directly to the sample. In alternative embodiments, the labeling element comprises an electronic medium for generating information required for the label and a method for printing the label that can be attached to the sample. In preferred embodiments, the labeling element is integrated with other elements of the instrument. In a specific embodiment, the labeling element is validated.

In a specific embodiment of this invention, the instruction element includes text and/or illustrative materials directing the practitioner how to use the labeling element so that the sample is properly collected, labeled, and directed to the laboratory. In a specific embodiment, the labeling element is integrated with the recording element so that there is a record that the sample has been obtained, processed and sent, and the status of the sample, test procedure, and test results can be tracked. In another specific embodiment, the labeling element is integrated with the certification element so that the laboratory receiving the sample is notified that an informed consent has been obtained for the specific test and that a prescription has been provided by the practitioner.

In a preferred embodiment of this invention the labeling element encodes the identity of the individual to preserve their privacy and confidentiality. This may involve attaching a label to the sample that has personal information encoded or in a form such as a barcode or personal identification number that is not readily identifiable except to those with appropriate authorization.

The billing element comprises forms required for direct payment by the individual or forms required to obtain reimbursement or arrange payment by a third party payor. Such elements are commonly known in the art and may comprise forms to be completed by the individual and/or the practitioner with a credit card number, insurance policy number, and billing codes. Alternatively these forms may comprise electronic medium or an interactive electronic medium designed to print a form with information from the individual or practitioner. In the preferred embodiment the billing element is integrated with other elements of the instrument.

The recording element comprises materials designed to be placed in an appropriate personal medical records maintained by the practitioner, provided to the individual for their own records, and deposited in other records as may be required, for example, by the practitioner, payor, or regulations The recording element constitutes the legal record of the informed consent process, providing a record of the procedures used to obtaining the consent, including, for example, information provided to the individual and any assessment that is performed, documentation of the test that is to be performed and any restrictions on the use of the information or sample, and certification of the informed consent. The process of maintaining medical records is known in the art and may involve printed materials or electronic medium. In the preferred embodiment, the recording element is integrated with other elements of the instrument. In specific embodiments the recording element may incorporate one or more of the following: a checklist documenting the procedures for informed consent that were used by the practitioner from the instruction element, the personal medical history and family history of the individual from the collection element, the informed consent and prescription from the certification element, information used to label the sample from the labeling element, and information for billing from the billing element.

In preferred embodiments, one or more than one of the elements of the instrument are designed so that information entered into one element is also incorporated into the recording element in a form suitable for incorporation in the medical record or provided to the individual. In a preferred embodiment these copies comprise printed materials and the design of the integrated instrument enables these pages to be physically separated from their respective elements and the complete instrument for inclusion in the record. In alternative embodiments, the instrument is designed so that carbon copies of essential information are imprinted on the recording element, for example, responses or scores from the assessment instrument, the prescription provided by the practitioner, or the checklist used by the practitioner may be copied directly onto a recording element in carbon copy. Informed consent must be generally completed in several copies including one that is given to the individual and one that becomes part of the individual's record. In a specific embodiment the recording element incorporates a copy of the certification element (informed consent document). In an alternative embodiment, these copies comprise electronic medium that can produce materials for inclusion in the record in either printed material or electronic medium.

The recording element will commonly contain other information to identify the individual including a medical record number, information on the referring practitioner, information on payors, information on the disposition of the sample, whether DNA has been banked, restrictions on the use of the sample and banked DNA, restrictions on the use of personal information, and directions on how to contact the individual or their practitioner with the test results. State and federal laws set standards for the protection of genetic information in individual medical records. The recording element also incorporates codes, mechanisms, procedures, and physical barriers, or fire walls necessary to protect the privacy of such information. For example, patient information may be represented in bar code or personal identifying code, de-identified, or encrypted. Methods and procedures for protecting the privacy of individual medical records are well known to those skilled in the art. This invention specifically provides for the individual to provide necessary releases in the certification element as may be required by law for the dissemination of information entered into the recording element to practitioners or others authorized by the individual.

The training element comprises text and illustrative materials designed to train practitioners in the use of the instrument for obtaining informed consent and methods for obtaining informed consent using said instruments. Materials designed for use in medical education and Continuing Medical Education (CME) are known in the art and frequent comprise printed materials, electronic medium, or mixed medium, for example, including books, CDs, web sites, pamphlets, slides, presentations. The element may comprise curriculum to be used in medical education or CME as well as illustrative materials that can be used in training and education. In a preferred embodiment, materials used to train practitioners in the use of the instrument are integrated with the integrated with instrument, for example, by describing the composition or methods of using the instrument, incorporating information, text or illustrative materials from the instrument, diagrams or incorporating representations of the instrument itself.

The quality control element comprises a reporting form that is used to determine whether performance specifications are being met by the practitioner using the instrument in the field. This element contains information about the process used to obtain informed consent that can be used for a review of the performance of the instrument and the practitioner. A specific utility of this invention is the standardization and validation of procedures for obtaining informed consent. There is also provided with this invention a method for performing quality assessment and quality control of the informed consent process using the quality control element. This method involves the reporting and review of results from the assessment element to determine whether performance specifications are being achieved in the field by different practitioners using the instrument in different populations and healthcare settings. The method may involve analysis of test results from random or selected regions or populations, instruments dealing with specific tests, the specialty or subspecialty of the practitioner, the language of the instrument, or the health, language, ethnic origin, or socioeconomic status of the individual. The results of such analysis can be used to measure the performance of individual practitioner against performance specifications or to further refine the integrated instrument, for example through modifications of the instruction element or modifications of a training element. The quality control element is integrated with other elements of the instrument. For example, the instruction element may inform the practitioner concerning quality control procedures, and the quality control element may incorporate data from the assessment element and the recording element.

The indemnification element certifies that the methods and instruments described in this invention were used to obtain consent and that these methods are validated and may provide indemnification against claims related to the adequacy of the informed consent process. The failure to obtain a proper informed consent may render a practitioner liable to legal action on the part of the individual or government regulatory body governing medical practice claiming that the individual was not adequately informed prior to certifying their consent or a test being performed. Use of the integrated and validated instruments and methods of this invention as described herein is designed to achieve certain performance specifications and standards including a minimum level of retention and understanding of information concerning the genetic test by the individual and the effective handling of the sample and genetic information.

The indemnification element documents the procedures that were used by the practitioner to obtain informed consent. The indemnification element is integrated with other elements of the instrument. For example, the indemnification element may incorporate elements of the information element to document the information that was provided to the individual, may incorporate a checklist from the instruction element to document that procedure were followed, may incorporate the results of the assessment element to demonstrate that a requisite level of retention and understanding was observed, and may incorporate the certification element to establish that the individual certified their consent. The indemnification element may be incorporated in the recording element and maintained with the individual's medical record, or filed with a central facility. In a further aspect of this invention, practitioners filing an indemnification element documenting their effective use of the instrument may receive indemnification against claims related to the adequacy of the informed consent process.

Some exemplary instruments are described below. These are provided for the purpose of illustrating the invention and are not intended to limit its scope.

Integrated Instruments Containing an Information Element

In a preferred embodiment of this invention, the instrument contains an information element integrated with an instruction element and a certification element, and with one or more than one of the following, optionally integrated, elements: a collection element, an assessment element, a labeling element, a billing element, a recording element, a training element, a quality control element and an indemnification element. In another embodiment, this instrument contains an integrated information element, an integrated instruction element and an integrated certification element, optionally integrated with two, three, four, five, six, seven or eight of the elements set forth above.

Integrated Instrument Containing an Assessment Element

In a preferred embodiment of this invention, the instrument contains an instruction element integrated with an information element and a certification element and further contains an optionally integrated assessment element. In another embodiment, this instrument also contains an optionally integrated collection element. In yet another embodiment, this instrument additionally contains one or more than one of the following, optionally integrated elements: a labeling element, a billing element, a recording element, a training element, a quality control element and an indemnification element. In another embodiment, this instrument contains an instruction element integrated with an information element and a certification element and optionally integrated with two, three, four, five, six, seven or eight of the elements set forth above.

Integrated Instrument Containing a Collection Element

In a preferred embodiment of this invention, the instrument contains an information element, instruction element and certification element, optionally integrated with a collection element. In another embodiment, this instrument contains in addition one or more than one of the following integrated elements: an assessment element, a labeling element, a billing element, a recording element, a training element, a quality control element and an indemnification element. In yet another embodiment, this instrument contains an integrated information element, integrated instruction element, integrated certification element and an integrated collection element, optionally integrated with two, three, four, five, six, seven or eight of the elements set forth above.

Integrated Instrument Containing a Collection Element and an Assessment Element

In a preferred embodiment of this invention, the instrument contains a certification element integrated with an instruction element, with an information element and with a collection element and an assessment element. Additionally, this embodiment may further include one or more than one of the following optionally integrated elements: a labeling element, a billing element, a recording element a training element, a quality control element and an indemnification element. In a specific embodiment of this invention, the instrument contains a certification element integrated an instruction element, an information element, a collection element and an assessment element, and optionally integrated with two, three, four, five, six, or seven of the elements listed above.

Training Element, Quality Control Element, and Indemnification Elements

A preferred embodiment of this invention is an instrument for obtaining informed consent containing an integrated training element. In such embodiment, the training element is integrated with the instruction element, the information element and the certification element. In an alternative embodiment, the training element is integrated with these three element and with an assessment element or a collection element, or both assessment and collection elements. In another alternative embodiment, the training element is integrated with these three elements and with one or more of the following optionally integrated elements: recording element, labeling element, billing element, quality control element, and indemnification element.

A specific object of this invention is an instrument for obtaining informed consent containing an integrated quality control element. In such embodiment, the quality control element is integrated with the instruction element, the information element and the certification element. In an alternative embodiment, the quality control element is integrated with these three element and with an assessment element or a collection element, or both assessment and collection elements. In another alternative embodiment, the quality control element is integrated with these three elements and with one or more of the following elements: recording element, labeling element, billing element, training element, and indemnification element. In a preferred embodiment, the quality control element is integrated with these three elements and with the reporting element. In a preferred embodiment, the quality control element is integrated with these three elements and with the training element. In further embodiments, the quality control element is integrated with two or more than two of the collection element, the assessment element, the recording element, the labeling element, the billing element, the training element and the indemnification element.

A specific object of this invention is an instrument for obtaining informed consent integrated with an indemnification element. In such embodiment, the indemnification element is integrated with the information element, the instruction element and the certification element. In an alternative embodiment, the indemnification element is integrated with these three elements and an assessment element or a collection element or with both of these elements. A specific embodiment is the integration of the indemnification element with these three elements and one or more than one of the assessment element, the collection element, the quality control element, the labeling element, the billing element, the recording element, and the training element. In a preferred embodiment the indemnification element incorporates a checklist from the instruction element. In a preferred embodiment the indemnification element incorporates the assessment element and the certification element.

Integrated and Validated Instrument

A preferred embodiment of this invention is a validated instrument for obtaining informed consent comprising the following integrated elements:
(a) an information element for an individual concerning a genetic test for one gene, more than one gene, related genes, a clinical outcome or a gene screen;
(b) an instruction element that can be used by a practitioner in providing instruction to the individual and guidance in the use of the instrument and obtaining informed consent;
(c) a collection element of information concerning the individual's personal medical history or their family medical history;
(d) an assessment element of the individual's retention or comprehension of said information;
(e) a certification element of the individual's consent for said test;
(f) a labeling element for labeling a sample or sample collection device obtained for genetic testing with the identity of the individual;
(g) a billing element either for direct payment by the individual or through a reimbursement agency; and
(h) a recording element that can be attached to the individual's medical record.

A specific embodiment of this invention is a validated instrument for obtaining informed consent that contains two or more of the following, optionally integrated, elements, an information element, an instruction element, a collection element, an assessment element, a certification element, a labeling element, a billing element, a recording element, a training element, a quality control element, and a indemnification element. In such embodiments, the instrument contains two, three, four, five, six, seven, eight, nine, or ten of these elements. Another specific embodiment of this invention is a validated instrument for obtaining informed consent that contains an instruction element integrated with one or more than one of the following elements: an information element, a collection element, an assessment element, a certification element, a labeling element, billing element, a recording element, a training element, a quality control element, and a indemnification element. In specific embodiment of this invention, the instrument contains a instruction element integrated with two, three, four, five, six, seven, eight or nine of said elements.

Integrated Instruments Useful in the Field of Medicine

A preferred embodiment of this invention is an instrument for obtaining consent for a genetic test for predicting a clinical outcome or determining the genetic risk of a clinical outcome, which instrument comprises the following integrated elements:
(a) an information element for an individual concerning a genetic test for one gene, more than one gene, related genes, associated with a clinical outcome;
(b) an instruction element that can be used by a practitioner in providing instruction to the individual and guidance in the use of the instrument and obtaining informed consent;
(c) a collection element of information concerning the individual's personal medical history or their family medical history;
(d) an assessment element of the individuals retention or comprehension of said information;
(e) a certification element of the individual's consent for said test;
(f) a labeling element for labeling a sample or sample collection device obtained for genetic testing with the identity of the individual;
(g) a billing element either for direct payment by the individual or through a reimbursement agency; and
(h) a recording element that can be attached to the individual's medical record.

A specific embodiment of this invention is an instrument for obtaining consent for a genetic test for predicting a clinical outcome or determining the genetic risk of a clinical outcome that contains an instruction element integrated with an information element and with a certification element, and optionally integrated with one or more than one of the following elements: a collection element, an assessment element, a labeling element, a billing element, a recording element, a training element, a quality control element, and an indemnification element. In specific embodiment of this invention, the instrument contains the integrated instruction, information and certification elements optionally integrated with two, three, four, five, six, seven, or eight of the other of the elements listed above.

C. Method of Use

There is provided by this invention a novel method for obtaining informed consent in which the practitioner uses an integrated instrument for obtaining such consent, more specifically a validated instrument. In specific embodiments, the method involves the use of an instrument with the following integrated elements: an information element, an instruction element, and a certification element, and optionally one or more elements selected from the group consisting of a collection element, an assessment element, a labeling element, a billing element, a recording element, a training element, a quality control element and an indemnification element. The method comprises completing a checklist of steps to obtain an informed consent using the instrument and the practitioner indicates on the checklist the steps that have been performed and completed. In a preferred embodiment, the method involves the steps of:
(a) procuring an integrated instrument for obtaining informed consent to a genetic test from an individual, which instrument contains an information element, an instruction element and a certification element;

(b) conveying to the individual information concerning the genetic test using the integrated information element;
(c) instructing an individual according to the directions contained in the integrated instruction element; and
(d) certifying the individual's consent for the test using the integrated certification element.

In addition, the method may include collecting a personal medical history and family history using an integrated collection element and may further or additionally include assessing the individual's retention or comprehension of the information using an integrated assessment element. Optionally, the method may further include the steps of labeling a sample with the identity of the individual using an integrated labeling element, and recording information concerning the informed consent process using an to integrated recording element.

In a preferred embodiment, the method further includes posting of one or more elements of an integrated instrument for obtaining informed consent. Posting makes the element or elements available as a resource to practitioners in printed or electronic medium (for example, on an Internet site or computer) or by incorporation of the element in policies, practices, guidelines, recommendations, training materials, or lessons. The posting of more than one element may be by the same or different means. For example, an instruction element may be posted in a procedure manual, and information elements provided as booklets to the individual, and recording elements provided as part of a medical record system. For example, an instruction element from an integrated instrument for obtaining informed consent may be posted with or without any of the additional elements included in the instruments and methods of the invention.

In detail, the step of "procuring" refers to obtaining an integrated instrument useful for obtaining informed consent for a specific gene, more than one related gene, a clinical outcome, or a gene screen. For example, an instrument may be procured by purchasing the instrument in written or electronic form, downloading the instrument from an Internet site, accessing the instrument on a computer, or printing it from a computer. Elements of the integrated instrument may be procured separately. For example, selected elements may be procured in written form, and others downloaded from an Internet site. Procuring also refers to the retrieval of elements that have been posted. Alternatively, one or more elements may be posted after they are procured by other means. Procuring may involve a payment for the instrument or one or more elements of the instrument or may be free of charge.

The step of "posting" of an element means to make it generally available to individuals or practitioners, for example by placing it on a web site, providing it as a resource in printed or electronic medium accessible to individuals or practitioners. Alternatively, posting may refer to policies, business practices, guidelines, recommendations, training materials, lessons that incorporate the use of one or more of said element.

The step of "conveying" refers to the delivery of an information element to an individual designed to give the individual with background information on a genetic test sufficient to provide an informed consent. For example, the individual can be given a booklet containing information about the genetic test or provided with access to an Internet site or computer with this information. Preferably conveying is performed using an information element integrated with one or more elements of the instrument.

The step of "instructing" refers to giving of instruction to an individual by a practitioner concerning a genetic test. Preferably, instructing is performed by the practitioner according to directions included in an instruction element integrated with one or more elements of the instrument.

The step of "collecting" refers to obtaining a personal medical history and family history from an individual. Preferably, collecting is performed using a worksheet and instructions included in a collection element integrated with one or more elements of the instrument.

The step of "assessing" refers to an assessment of an individual's retention or comprehension of information sufficient to provide an informed consent by presenting the individual with questions concerning aspects of the test and testing process and scoring their responses. Preferably assessing is performed using an assessment element integrated with one or more elements of the instrument element integrated with one or more elements of the instrument.

The step of "certifying" refers to the completion of a legal informed consent document by an individual and appropriate witnesses. Preferably certifying is performed using a certification element integrated with one or more elements of the instrument.

The step of "labeling" refers to the labeling of a sample with information required for the proper handling of the sample, performance of the test, and protection of individual privacy. Preferably, labeling is performed using a labeling element integrated with one or more elements of the instrument.

The step of "recording" refers to the placement of essential information concerning the informed consent process and the individual's medical and family history in a medical record. Preferably recording is performed using a recording element integrated with one or more elements of the instrument. Indemnifying refers to the issuance of an insurance policy which pays for claims against the practitioner related to the quality of the informed consent obtained using the instrument.

Sample Collection and Diagnostic Devices

An additional embodiment of this invention is kit comprising a sample collection device and an integrated instrument for obtaining informed consent for a genetic test. Sample collection devices are known in the art. Samples can be collected using routine procedures from blood drawing and tubes that enable the separation of white blood cells (that contain DNA) from red blood cells, serum, or plasma. Specialized devices are also known in the art and approved by the FDA for sample collection. The OraSure Oral Specimen Collection Device from Orasure Technologies, Inc. is one example of an FDA-approved sample collection device that can be used for the collection of DNA from the oral mucosa for clinical applications. Another example is S&S 903 Specimen Collection Paper from Schleicher & Schuell, GmbH is another FDA listed device that is widely used for adult sample collection, including genetic studies. S&S 903 Specimen Collection Paper, is used widely for newborn screening and has also been used for genetic studies. S&S 903 Specimen Collection Paper has also been incorporated into single and multi-part forms and forms and customized printing is available from the manufacturer with biologically inactive inks and glues that enable the paper to incorporate information or codes for patient identification, processing, and lot traceability. The 903 device can be used to collect blood or body fluids such as urine, tears, or saliva that are spotted and dried onto the 903 paper. In this form the sample is stable and can be mailed to centralized labs for analysis, sample extraction, or DNA banking.

An additional embodiment of this invention is kit comprising a sample collection device and an integrated instrument for obtaining informed consent for a genetic test. In one example, the sample collection device is printed S&S 903 paper that is included as part of the labeling element of the integrated instrument. Alternatively, the sample collection device may be included in the recording element and may be comprised of a multi-part form comprising S&S 903 paper for sample collection. In a preferred example, a booklet comprising one or more of the elements of the integrated element may contain a page made of S&S 903 paper which is perforated or glued to the booklet for easy separation. The booklet may be constructed such that information concerning the individual's identity, the test to be performed, handling of the sample and test results, and valid certification of consent for DNA banking and testing is entered simultaneously onto a sample collection device such as S&S903 paper and onto other elements of the instrument, for example, by constructing the instrument such that carbon copies are made on one or more elements such as the checklist within the instruction element, the labeling element, or certification element. In another preferred example, sample collection device, for example, S&S 903 paper, may be integrated with other elements of the instrument, by describing the process for sample collection in the information element or directions for obtaining and processing a sample in the instruction element. It will be recognized by those skilled in the art that other sample collection devices may be integrated with the instrument for informed consent in an analogous manner.

EXAMPLE 1

Examples of Genetic Tests

A. Genetic Tests Predicting the Risk of Common Disease.

Most common diseases are considered to be multifactorial or polygenic, meaning that many different genes may contribute to the risk of the disorder. Examples include:

| Disorder | Genetic test |
|---|---|
| Cancer | Breast Cancer (BRCA1 )*; BRCA1; Ovarian Cancer (BRCA1) |
| | Breast Cancer (BRCA2)*; BRCA2; Ovarian Cancer (BRCA2) |
| | p53, p21, p16 |
| | Ataxia Telangectasia |
| | NHPCCm FAP (colon cancer) |
| | Medullary Thyroid Carcinoma; MTC |
| | Alzheimer's Disease    Apolipoprotein E |
| | amyloid precursor protein |
| | presenilin-1, presenilin-2 |
| | 2-macroglobulin |
| | alpha 1-antichymotrypsin |
| Heart attack, stroke | Apolipoprotein E |
| | Lipoprotein lipase |
| | LDL receptor |
| | MTHFR |
| | Angiotensinogen |
| ALS | Superoxide Dismutase (SOD) |
| COPD | alpha 1-antitrypsin (AAT) |
| Anemia | hemoglobin S |
| | hemoglobin C |
| | thalassemia (alpha) |
| | thalassemia (beta) |
| | G-6 PD |
| Liver failure | Hemochromatosis |
| Spina Bifida | MTHFR |
| Arthritis | HLA-B, HLA-D |
| Periodontal disease | IL-1 |
| Osteoporosis | col1A1 |

B. Genetic Tests Predictive of Drug Response.

Variations in genes that affect the metabolism of drugs can increase drug levels, drug toxicity and drug interactions. Genetic tests can be used to avoid drugs that have a higher probability of toxicity and individualize the dose to maximize the therapeutic benefit while minimizing toxicity. Examples include:

| Gene test | Drugs and chemical affected |
|---|---|
| CYP1A1 | Chlorinated benzenes (environmental toxin) |
| CYP1A2 | Caffeine, phenacetin, warfarin, Erythromycin, Ropivacaine, Haloperidol, antipyrine, theophylline, Paracetamol |
| CYP2C8 | TCA, Diazepam, Hexabarbitone |
| CYP2C9/10 | Phenytoin, S-warfarin, Diclofenac, Tolbutamide |
| CYP2C19 | Mephenytoin, Diazepam (Valium), TCA |
| CYP2D6 | Debrisoquine, Codeine, Dextrometorphan, b-blockers, SSRIs, others |
| CYP2E1 | Paracetamol, Isoflurane, Sevoflurane, Methoxyflurane, Enflurane, |
| CYP3A4 | Nifedipine, Dextrometorphan, Alfentanil, Sufentanil, Fentanyl, Erythromycin, Lignocaine, Ropivacaine, Midazolam, Codeine, Granisetron, Hydrocortisone |
| CYP3A5 | Caffeine, Diltiazem |
| CYP3A7 | Midazolam |
| CYP17 | Pregnolone |
| CYP19 | Testosterone |
| CYP21A2 | 17-hydroxyprogesterone |

C. Variations in Genes that Affect Drug Targets and Drug Response May Affect the Safety and Efficacy of a Drug.

Genetic tests can be used to avoid drugs that have a higher probability of toxicity and individualize the dose to maximize the therapeutic benefit while minimizing toxicity. Examples include:

| Gene test | Drugs or chemicals affected |
|---|---|
| Factor V | Oral contraceptives |
| Prothrombin | Oral contraceptives |
| TPMT (thiopurine methyltransferase) | Azothioprine, mercaptopurine (purine analogues) |
| 5' lipoxegenase | Zilutin (5' lipoxegenase inhibitors) |
| CETP (cholesterol ester transfer protein) | Pravastatin, others (statins) |
| ApoE (apolipoprotein E) | Tacrine (cholinesterase inhibitors, muscarinic agonists, others) |
| G-6 PD | sulfur drugs |
| Pseudocholinesterase | pseudocholinesterase inhibitors |
| Beta-receptor | Isoproterenol (beta-agonists) |
| Serotonin transporter | SSRI antidepressants (Prozac, Pindolol, others) |
| Acetyltransferase | isoniazid, others |
| ADH(2h) (aldehyde dehydrogenase) | alcohol |
| ACE (angiotensin converting enzyme | Enalpril, others |
| Opioid receptors | Endorphins, morphine |

Genetic Tests for Inherited or Genetic Disorders.

A large number or inherited genetic diseases are caused by well-characterized mutations in genes that impair the function of a gene or cause a gene to have dominant, adverse effects. The following is partial list of genetic tests for diseases that are generally considered to be genetic or congenital.

DiGeorge Syndrome 2
Velocardiofacial Syndrome 2
1p36 Deletion Syndrome
22q11 Deletion Syndrome
Cayler Cardiofacial Syndrome
Conotruncal Anomaly Face Syndrome
DiGeorge Syndrome Opitz G/BBB
  Sedlackova Syndrome
  Shprintzen Syndrome
  Velocardiofacial Syndrome
3-Methylglutaconic Aciduria
46,XY Gonadal Dysgenesis
Achalasia-Addisonianism-Alacrima Syndrome
Achondrogenesis
  Achondrogenesis Type IA Achondrogenesis Type IB
  Achondrogenesis Type II
Achondroplasia
Acute Hepatic Porphyria
Acute Intermittent Porphyria
Adenosine Monophosphate Deaminase 1
Adrenoleukodystrophy, X-Linked
  Adrenomyeloneuropathy
Alagille Syndrome
Albinism
  Ocular Albinism, X-Linked
  Oculocutaneous Albinism
  Oculocutaneous Albinism Type 1
  Oculocutaneous Albinism Type 1A
    Oculocutaneous Albinism Type 1B
    Oculocutaneous Albinism Type 2 (P Related)
    Oculocutaneous Albinism Type 3 (TRP1 Related)
Aldosteronism, Sensitive to Dexamethasone
Alpha-1-Antitrypsin Deficiency
Alpha-Mannosidosis
Alpha-Thalassemia
Alpha-Thalassemia X-Linked Mental Retardation Syndrome
Alport Syndrome
  Alport Syndrome, Autosomal Dominant
  Alport Syndrome, Autosomal Recessive
  Alport Syndrome, X-Linked
Alzheimer Disease
  Early Onset Familial Alzheimer Disease
  Alzheimer Disease Type 1
  Alzheimer Disease Type 3
  Alzheimer Disease Type 4
  Late-Onset Familial Alzheimer Disease
  Alzheimer Disease Type 2
  Alzheimer Disease Type 5
Amino Adipic Aciduria
Amyotrophic Lateral Sclerosis
Androgen Insensitivity Syndrome
  Complete Androgen Insensitivity Syndrome
  Mild Androgen Insensitivity Syndrome
  Partial Androgen Insensitivity Syndrome
Angelman Syndrome
Anhaptoglobinemia
Aniridia
Ankyloblepharon-Ectodermal Defects-Cleft Lip/Palate
Ankylosing Spondylitis
Apolipoprotein E Genotyping
Apparent Mineralocorticoid Excess Syndrome
Argininemia
Argininosuccinicaciduria
Aromatic L-Amino Acid Decarboxylase Deficiency
Aspartylglycosaminuria
Atelosteogenesis Type II
Autoimmune Polyendocrinopathy Syndrome Type 1
Autosomal Recessive Adrenoleu kodystrophy
Autosomal Recessive Congenital lchthyosis
  Congenital lchthyosiform Erythroderma
  Non-Bullous Congenital lchthyosiform Erythroderma
Avellino Corneal Dystrophy
Barth Syndrome
Beckwith-Wiedemann Syndrome
Beta-Mannosidosis
Beta-Methylcrotonylglycinuria
Beta-Thalassemia
  Thalassemia Intermedia
  Thalassemia Major
  Thalassemia Minor
Biotin-Responsive Multiple Carboxylase Deficiencies
  Biotinidase Deficiency
  Holocarboxylase Synthetase Deficiency
Bloom Syndrome
Breast Cancer Genetics
BRCA1 and BRCA2 Hereditary Breast/Ovarian Cancer
  BRCA1 Hereditary Breast/Ovarian Cancer
  BRCA2 Hereditary Breast/Ovarian Cancer
Brugada Syndrome
CADASIL
Camurati-Engelmann Disease
Canavan Disease
Carbamoylphosphate Synthetase I Deficiency
Carney Complex
Carnitine Deficiency, Systemic
Carnitine Palmitoyltransferase IA (liver) Deficiency
Carnitine Palmitoyltransferase II Deficiency
Carnitine-Acylcarnitine Translocase Deficiency
Cartilage-Hair Hypoplasia
Catecholaminergic Ventricular Tachycardia
Catecholaminergic Ventricular Tachycardia, Dominant
Catecholaminergic Ventricular Tachycardia, Recessive
Celiac Disease
Cerebrotendinous Xanthomatosis
Charcot-Marie-Tooth Disease, Type 4B
Charcot-Marie-Tooth Hereditary Neuropathy
  Charcot-Marie-Tooth Neuropathy Type 1
  Charcot-Marie-Tooth Neuropathy Type 1A
  Charcot-Marie-Tooth Neuropathy Type 1B
  Dejerine-Sottas Disease
  Charcot-Marie-Tooth Neuropathy Type 1C
  Charcot-Marie-Tooth Neuropathy Type 1D
  Charcot-Marie-Tooth Neuropathy Type 2
  Charcot-Marie-Tooth Disease, Neuronal/Axonal
  Charcot-Marie-Tooth Neuropathy Type 2A
  Charcot-Marie-Tooth Neuropathy Type 2B
  Charcot-Marie-Tooth Neuropathy Type 2C
  Charcot-Marie-Tooth Neuropathy Type 2D
  Charcot-Marie-Tooth Neuropathy Type 2E
  Charcot-Marie-Tooth Neuropathy Type 4
  Charcot-Marie-Tooth Neuropathy Type 4A
  Charcot-Marie-Tooth Neuropathy Type 4B
  Charcot-Marie-Tooth Neuropathy Type 4C
  Charcot-Marie-Tooth Neuropathy Type 4D
  Charcot-Marie-Tooth Neuropathy Type 4E
  Charcot-Marie-Tooth Neuropathy Type 4F
  Dejerine-Sottas Disease
  Charcot-Marie-Tooth Neuropathy Type X
  Hereditary Neuropathy with Liability to Pressure Palsies
CHILD Syndrome
Chondrodysplasia Punctata, X-Linked Dominant
Choroideremia
Citrullinemia
Clinical Confirmation of Mutations Identified in Research
  Labs Cockayne Syndrome
  Cockayne Syndrome Type A
  Cockayne Syndrome Type B
  Cockayne Syndrome Type I
  Cockayne Syndrome Type II
  Cockayne Syndrome Type III
  Xeroderma Pigmentosa-Cockayne Syndrome
Coffin-Lowry Syndrome
Congenital Adrenal Hyperplasia
  11 beta Hydroxylase Deficiency
  17 alpha Hydroxylase Deficiency 21-Hydroxylase Deficiency
3 beta Hydroxysteriod Dehydrogenase Deficiency
Cholesterol Desmolase Deficiency
Congenital Contractural Arachnodactyly
Congenital Disorders of Glycosylation
Congenital Erythropoietic Porphyria
Congenital Hypomyelination
Congenital Insensitivity to Pain with Anhidrosis
Congenital Muscular Dystrophy
Congenital Muscular Dystrophy with Cerebellar Hypoplasia
Congenital Muscular Dystrophy with Early Spine Rigidity
Congenital Muscular Dystrophy with Integrin alpha 7 Mutations
Congenital Muscular Dystrophy with Merosin Deficiency
Congenital Muscular Dystrophy with Mitochondrial Structural Abnormalities
   Congenital Muscular Dystrophy, Merosin-Positive
   Fukuyama Muscular Dystrophy
   Muscle-Eye-Brain Disease
   Walker-Warburg Syndrome
Coronal Synostosis
Coronary Artery Disease Risk Factor (ACE)
Coronary Artery Disease Risk Factor (PLA1/2)
Craniosynostosis
   FGFR-Related Craniosynostosis Syndromes
FGFR1-Related Craniosynostosis SyndromePfeifferSyndrome Type 1, 2, and 3
FGFR2-Related Craniosynostosis Syndromes
   Apert Syndrome
   Beare-Stevenson Syndrome
   Crouzon Syndrome
   Jackson-Weiss Syndrome
   Pfeiffer Syndrome Type 1, 2, and 3
   FGFR3-Related Craniosynostosis Syndromes
Crouzon Syndrome with Acanthosis Nigricans
   Muenke Syndrome
Cri du Chat Syndrome
Cystic Fibrosis
   Congenital Bilateral Absence of the Vas Deferens
Cystinosis
   Intermediate Cystinosis
   Nephropathic Cystinosis
   Non-Nephropathic Cystinosis
Cystinuria
Cytochrome C Oxidase Deficiency
Darier Disease
Diabetes Mellitus, Noninsulin-Dependent
Diabetes Mellitus, Transient Neonatal
Diastrophic Dysplasia
Disorders of Galactose Metabolism
   Galactokinase Deficiency
   Galactose Epimerase Deficiency
   Galactosemia
Variant Galactosemias Duarte VariGalactosemia
Disorders of Phenylalanine Metabolism
Phenylalanine Hydroxylase Deficiency
   Non-PKU Hyperphenylalanemia
   Phenylketonuria
   Variant PKU
   Tetrahydrobiopterin deficiencies
6-Pyruvoyl-Tetrahydropterin Synthase Deficiency
Dihydropteridine Reductase Deficiency (DHPR)
   GTP Cyclohydrolase-1 Deficiency (GTPCH)
   Pterin-4a Carbinolamine Dehydratase Deficiency
   Tetrahydrobiopterin deficiencies
   GTP Cyclohydrolase 1-Deficient DRD
   Sepiapterin Reductase Deficiency (SR)
Dopa-Responsive Dystonia
   GTP Cyclohydrolase 1-Deficient DRD
   Tyrosine Hydroxylase-Deficient DRD
Down Syndrome Critical Region
Dubin-Johnson Syndrome
Dystrophinopathies
   Duchenne/Becker Muscular Dystrophy
      Becker Muscular Dystrophy
      Duchenne Muscular Dystrophy
   X-Linked Dilated Cardiomyopathy
Early-Onset Primary Dystonia
Ectrodactyly, Ectodermal Dysplasia, and Cleft Lip/Palate Syndrome
Ehlers-Danlos Syndrome, Arthrochalasia Type
Ehlers-Danlos Syndrome, Kyphoscoliotic Form
Ehlers-Danlos Syndrome, Vascular Type
Emery-Dreifuss Muscular Dystrophy
Epidermolysis Bullosa Dystrophica, Bart Type
Epidermolysis Bullosa Dystrophica, Cockayne-Touraine Type Epidermolysis Bullosa Dystrophica, Hallopeau-Siemens Type Epidermolysis Bullosa Dystrophica, Inversa Type
Epidermolysis Bullosa Dystrophica, Pasini Type
Epidermolysis Bullosa Junctional, Disentis Type
Epidermolysis Bullosa Junctional, Herlitz-Pearson Type
Epidermolysis Bullosa Letalis with Pyloric Atresia
Epidermolysis Bullosa Simplex
Epidermolysis Bullosa Simplex with Mottled Pigmentation
Epidermolysis Bullosa Simplex, Dowling-Meara Type
Epidermolysis Bullosa Simplex, Koebner Type
Epidermolysis Bullosa Simplex, Recessive
Epidermolysis Bullosa Simplex, Weber-Cockayne Type
Epidermolysis Bullosa with Muscular Dystrophy
Epidermolysis Bullosa, Pretibial
Epidermolytic Hyperkeratosis
Epidermolytic Palmoplantar Keratoderma
Erythrokeratodermia Variabilis
Erythropoietic Protoporphyria
Ethylmalonic Encephalopathy
Fabry Disease
   Cardiac Variant Fabry Disease
   Classic Fabry Disease
Facioscapulohumeral Muscular Dystrophy
Familial Atypical Mycobacteriosis
Familial Colon Cancer Syndromes
   Colon Cancer (APC 11307K related)
   Familial Adenomatous Polyposis
      Attenuated FAP
      Gardner Syndrome
      Turcot Syndrome
   Hereditary Non-Polyposis Colon Cancer
   Turcot Syndrome
   Juvenile Polyposis Syndrome
   PTEN Hamartoma Tumor Syndrome (PHTS)
   Bannayan-Riley-Ruvalcaba Syndrome
   Cowden Syndrome
   Proteus Syndrome
   Proteus-Like Syndrome
   Peutz-Jeghers Syndrome
Familial Combined Hyperlipidemia
Familial Dysautonomia
Familial Hemiplegic Migraine
   Familial Hemiplegic Migraine 1
   Familial Hemiplegic Migraine 2
Familial Hibernia Fever
Familial Lipoprotein Lipase Deficiency
Familial Malignant Melanoma Familial Mediterranean Fever
Fanconi Anemia
Farber Disease
Fatty Acid Oxidation Disorder, Unspecified
Fragile X Syndrome
FRAXE Syndrome
Frontotemporal Dementia
Amyotrophic Lateral Sclerosis/Frontotemporal Dementia
    Frontotemporal Dementia with Parkinsonism-17
Disinhibition-Dementia-Parkinsonism-Amyotrophy
    Familial Pick's Disease
    Wilhelmsen-Lynch Disease
    Progressive Supranuclear Palsy
Fructose 1,6 Bisphosphatase Deficiency
Fucosidosis
Fumarate Hydratase Deficiency
Gaucher Disease
    Gaucher Disease Type 1
    Gaucher Disease Type 2 (Acute)
    Gaucher Disease Type 3 (Subacute/Chronic)
    Gaucher Disease, Cardiovascular Form
    Gaucher Disease, Perinatal-Lethal Form
Genotypic Gender Assignment
Gilbert Syndrome
Gliosis, Familial Progressive Subcortical
Glutaricacidemia Type 2
Glycerol Kinase Deficiency
Glycogen Storage Disease Type Ia
Glycogen Storage Disease Type Ib
Glycogen Storage Disease Type II
Glycogen Storage Disease Type III
Glycogen Storage Disease Type IV
Glycogen Storage Disease Type IX
Glycogen Storage Disease Type V
Glycogen Storage Disease Type VI
Glycogen Storage Disease Type VII
Glycoprotein 1a Deficiency
GM1 Gangliosidosis
GM2 Gangliosidoses (Hexosaminidase A- and B-Deficient)
    Sandhoff Disease
Granular Corneal Dystrophy
Greig Cephalopolysyndactyly Syndrome
Guanidinoacetate Methyltransferase Deficiency
Hailey-Hailey Disease
Hallervorden-Spatz Syndrome
Hartnup Disease
Hemoglobin C
Hemoglobin Constant Spring
Hemoglobin D
Hemoglobin E
Hemoglobin O
Hemoglobin S
Hemophilia A
Hemophilia B
Hereditary Angioneurotic Edema
Hereditary Ataxias
    Autosomal Dominant Hereditary Ataxias DRPLA
    Episodic Ataxia Type 1
    Episodic Ataxia Type 2
    Spinocerebellar Ataxia Type 1
    Spinocerebellar Ataxia Type 2
    Spinocerebellar Ataxia Type 3
    Spinocerebellar Ataxia Type 4
    Spinocerebellar Ataxia Type 5
    Spinocerebellar Ataxia Type 6
    Spinocerebellar Ataxia Type 7
    Spinocerebellar Ataxia Type 8
    Spinocerebellar Ataxia Type 10
    Spinocerebellar Ataxia Type12
    Autosomal Recessive Hereditary Ataxias
        Ataxia with Oculomotor Apraxia
        Ataxia with Oculomotor Apraxia 1
        Ataxia with Oculomotor Apraxia 2
        Ataxia with Vitamin E Deficiency (AVED)
        Ataxia-Telangiectasia
        Autosomal Recessive Spastic Ataxia of Charlevoix-Saguenay
        Friedreich Ataxia
    FRDA1
    FRDA2
    Infantile Onset Spinocerebellar Ataxia (IOSCA)
        Marinesco-Sjogren Syndrome
    Mitochondrial Disorders with Ataxia
    MERF
    NARP
X-Linked Recessive Hereditary Ataxias
    Sideroblastic Anemia and Ataxia
Hereditary Coproporphyria
Hereditary Diffuse Gastric Cancer
Hereditary Fructose Intolerance
Hereditary Hearing Loss and Deafness
    Nonsyndromic Hearing Loss and Deafness
    Nonsyndromic Hearing Loss and DeafnessAminoglycoside-Induced Deafness
    Nonsyndromic Hearing Loss and Deafness, Autosomal Dominant
    DFNA 3 (Connexin 26)
    Nonsyndromic Hearing Loss and Deafness, Autosomal Recessive
    DFNB 1 (Connexin 26)
    Nonsyndromic Hearing Loss and Deafness, X-Linked
Syndromic Hearing Loss and Deafness
    Mitochondrial Disorders
    Diabetes and Hearing Loss
    Kearns-Sayre Syndrome
    MELAS
    MERRF
    NARP
Syndromic Hearing Loss and Deafness, Dominant
    Alport Syndrome, Autosomal Dominant
    Branchiootorenal Syndrome
    Neurofibromatosis 2
    Stickler Syndrome
        Stickler Syndrome Type I
        Stickler Syndrome Type II
        Stickler Syndrome Type III
    Waardenburg Syndrome
        Waardenburg Syndrome Type II
        Waardenburg Syndrome Type III
        Waardenburg Syndrome Type IV
Syndromic Hearing Loss and Deafness, Recessive
    Alport Syndrome, Autosomal Recessive
    Jervell and Lange-Nielsen Syndrome
    LQT 1
    LQT 5
    Pendred Syndrome
    Refsum Disease
        Refsum Disease, Adult
        Refsum Disease, Infantile
    Usher Syndrome
        Usher Syndrome Type 1
        Usher Syndrome Type 2
        Usher Syndrome Type 3
Syndromic Hearing Loss and Deafness, X-Linked
    Alport Syndrome, X-Linked
    DFN 1
    Norrie Disease
X-Linked Familial Exudative Vitreoretinopathy
Hereditary Hemochromatosis
Hereditary Hemorrhagic Telangiectasia
    Hereditary Hemorrhagic Telangiectasia Type 1
    Hereditary Hemorrhagic Telangiectasia Type 2

Hereditary Inclusion Body Myopathy 2
Hereditary Multiple Exostoses
    Multiple Exostoses Type I
    Multiple Exostoses Type II
Hereditary Pancreatitis
Hereditary Sensory and Autonomic Neuropathy 11
Hereditary Sensory Neuropathy Type I
Hereditary Spastic Paraplegia
    Hereditary Spastic Paraplegia, Dominant
    Hereditary Spastic Paraplegia, Complicated
    SPG 9
    Hereditary Spastic Paraplegia, Uncomplicated
SPG 3
    SPG 4
    SPG 6
    SPG 8
    SPG10
    SPG12
    SPG13
    Hereditary Spastic Paraplegia, Recessive
    Hereditary Spastic Paraplegia, Complicated
    SPG 7
    Hereditary Spastic Paraplegia, Uncomplicated
    SPG 5
    SPG 11
    Hereditary Spastic Paraplegia, X-Linked
Pelizaeus-MerzbacherDisease/Spastic Paraplegia
Spastic Paraplegia 1
Hermansky-Pudlak Syndrome
HPS1
    HPS2
    HPS3
Hexosaminidase A Deficiency
Chronic and Adult-Onset Hexosaminidase A Deficiency
    Juvenile (Subacute) Hexosaminidase A Deficiency
    Tay-Sachs Disease
Hidrotic Ectodermal Dysplasia 2
Holoprosencephaly
Nonsyndromic Holoprosencephaly, Autosomal Dominant
    Holoprosencephaly 2
    Holoprosencephaly 3
    Holoprosencephaly 4
    Holoprosencephaly 5
Syndromic Holoprosencephaly, Autosomal Dominant
    Ectrodactyly and hypertelorism
    Martin Syndrome
    Pallister-Hall Syndrome
    Rubinstein-Taybi Syndrome
    Steinfeld syndrome
Syndromic Holoprosencephaly, Autosomal Recessive
    Facial clefts and brachial amelia
    Genoa Syndrome
    Hydrolethalus Syndrome
    Lambotte Syndrome
    Meckel-Gruber Syndrome
    Smith-Lemli-Opitz Syndrome
Homocystinuria
Huntington Disease
Hydrocephalus, X-Linked
Hyper IgD Syndrome
Hyperbilirubinemia, Rotor Type
Hyperekplexia
Hyperlipoproteinemia Type III
Hyperlysinemia
Hyperoxaluria, Primary, Type I
Hyperpipecolatemia
Hypochondroplasia
Hypohidrotic Ectodermal Dysplasia, Dominant
Hypohidrotic Ectodermal Dysplasia, Recessive
Hypohidrotic Ectodermal Dysplasia, X-Linked
Hypophosphatasia
Hypophosphatemic Rickets, Dominant
Hypophosphatemic Rickets, X-Linked
Ichthyosis Bullosa of Siemens
Ichthyosis, X-Linked
Identity Testing
    Parentage Testing
    Family Relatedness
    Maternity Testing
    Paternity Testing
    Zygosity Testing
Incontinentia Pigmenti
Kallmann Syndrome, X-Linked
Krabbe Disease
Lactate Dehydrogenase Deficiency
Langer Mesomelic Dwarfism
Langer-Giedion Syndrome
Lattice Corneal Dystrophy Type I
Lecithin Cholesterol Acyltransferase Deficiency
Leprechaunism
Leri-Weill Dyschondrosteosis
Lesch-Nyhan Syndrome
Li-Fraumeni Syndrome
Limb-Girdle Muscular Dystrophy
Limb-Girdle Muscular Dystrophies, Autosomal Dominant
    Bethlem Myopathy
    Caveolinopathy
    LGMD1A
    LGMD1B
Limb-Girdle Muscular Dystrophies, Autosomal Recessive
    Calpainopathy
    Dysferlinopathy
    Sarcoglycanopathies
        Alpha-Sarcoglycanopathy
        Beta-Sarcoglycanopathy
        Delta-Sarcoglycanopathy
        Gamma-Sarcoglycanopathy
    Telethoninopathy
Limb-Mammary Syndrome
Lissencephaly
Classic Lissencephaly and Subcortical Band Heterotopia (Agyria-Pachygyria-Band Spectrum)
    Baraitser-Winter Syndrome
    Isolated Lissencephaly/Subcortical Heterotopia
    X-Linked Lissencephaly/Subcortical Heterotopia
    17-Linked Lissencephaly/Subcortical Heterotopia
    Miller-Dieker Syndrome
    Cobblestone Dysplasia (Lissencephaly)
    Cobblestone Lissencephaly
    Muscle-Eye-Brain Disease
    Walker-Warburg Syndrome
    Lissencephaly Variants with Other Anomalies
    Microlissencephaly
Microcephaly with Simplified Gyral Pattern, Group
    Microlissencephaly I
    Microlissencephaly II
    Microlissencephaly III
Long Chain 3-Hydroxyacyl-CoA Dehydrogenase Deficiency
Long Chain Acyl-CoA Dehydrogenase Deficiency
Long QT Syndrome
    Jervell and Lange-Nielsen Syndrome
    LQT 1
    LQT5
    Long QT Syndrome, Dominant
    LQT 1
        LQT 2
        LQT 3
        LQT 4
        LQT 5
        LQT 6
Lowe Syndrome
Lymphoproliferative Disease, X-Linked
Malignant Hyperthermia Susceptibility
Marfan Syndrome Medium Chain 3-Ketothiolase Deficiency
Medium Chain Acyl-Coenzyme A Dehydrogenase Deficiency Menkes Disease
Mental Retardation Syndromes, Undiagnosed
Metachromatic Leukodystrophy
Metaphyseal Chondrodysplasia, Schmid Type
Mevalonicaciduria
Mitochondrial Disorders
   Chorea and Dementia
   Chronic Progressive External Ophthalmoplegia
   Diabetes and Hearing Loss
   Infantile Myopathy and Lactic Acidosis (Fatal and Non-Fatal Forms)
   Kearns-Sayre Syndrome
   Leber Hereditary Optic Neuropathy
   Leigh Syndrome (mtDNA mutation)
MELAS
   MERRF
   NARP
   Nonsyndromic Hearing Loss and Deafness
   Aminoglycoside-Induced Deafness
   Pearson Syndrome
Molybdenum Cofactor Deficiency
MTHFR Deficiency
Mucolipidosis I
Mucolipidosis II
Mucolipidosis IV
Mucopolysaccharidosis Type I
Mucopolysaccharidosis Type II
Mucopolysaccharidosis Type IIIA
Mucopolysaccharidosis Type IIIB
Mucopolysaccharidosis Type IIIC
Mucopolysaccharidosis Type IIID
Mucopolysaccharidosis Type IVA
Mucopolysaccharidosis Type IVB
Mucopolysaccharidosis Type VI
Mucopolysaccharidosis Type VII
Multiple Endocrine Neoplasia Type 1
Multiple Endocrine Neoplasia Type 2
   Familial Medullary Thyroid Carcinoma
   Multiple Endocrine Neoplasia Type 2A
   Multiple Endocrine Neoplasia Type 2B
Multiple Epiphyseal Dysplasia
Myoclonic Epilepsy of Unverricht and Lundborg
Myotonia Congenita, Dominant
Myotonic Dystrophy
   Myotonic Dystrophy Type 1
   Myotonic Dystrophy Type 2
Myotubular Myopathies
   Myotubular Myopathy, Dominant
   Myotubular Myopathy, Recessive
   Myotubular Myopathy, X-Linked
   Myotubular Myopathy Type 1
Narcolepsy
Nephrogenic Diabetes Insipidus
   Nephrogenic Diabetes Insipidus, Autosomal
   Nephrogenic Diabetes Insipidus, X-Linked
Nephronophthisis
   Nephronophthisis, Adolescent
   Nephronophthisis, Infantile
   Nephronophthisis, Juvenile
Netherton Syndrome
Neurofibromatosis 1
Neuronal Ceroid-Lipofuscinoses
   Neuronal Ceroid-Lipofuscinosis, Adult
   Neuronal Ceroid-Lipofuscinosis, Infantile
   Neuronal Ceroid-Lipofuscinosis, Juvenile
   Neuronal Ceroid-Lipofuscinosis, Late Infantile
     Neuronal Ceroid-Lipofuscinosis, Late Infantile
     Neuronal Ceroid-Lipofuscinosis, Finnish Variant
     Neuronal Ceroid-Lipofuscinosis, Gypsy/Indian, Early Juvenile Variant
     Neuronal Ceroid-Lipofuscinosis, Turkish variant
   Northern Epilepsy
Neutrophil Antigen Genotyping
Nevoid Basal Cell Carcinoma Syndrome
Niemann-Pick Disease Due to Sphingomyelinase Deficiency
   Niemann-Pick Disease Type A
   Niemann-Pick Disease Type B
   Niemann-Pick Disease Type C
   Niemann-Pick Disease Type C1
   Niemann-Pick Disease, Nova Scotia Type
   Niemann-Pick Disease Type C2
Nijmegen Breakage Syndrome
Non-Ketotic Hyperglycinemia
Nonepidermolytic Palmoplantar Hyperkeratosis
Noonan Syndrome
Oculopharyngeal Muscular Dystrophy
Organic Acidemias
   3-Hydroxy-3-Methylglutaryl-Coenzyme A Lyase
   Glutaricacidemia Type 1
   Isovaleric Acidemia
   Ketothiolase Deficiency
   Maple Syrup Urine Disease
     Maple Syrup Urine Disease Type 1A
     Maple Syrup Urine Disease Type 1B
     Maple Syrup Urine Disease Type 2
   Methylmalonic Aciduria
Methylmalonic Acidemia cb1C Variant
   Propionic Acidemia
Ornithine Transcarbamylase Deficiency
Osteogenesis Imperfecta Type I
Osteogenesis Imperfecta Type II
Osteogenesis Imperfecta Type III
Osteogenesis Imperfecta Type IV
Osteopetrosis, Autosomal Dominant, Type II
Pachyonychia Congenita
Paget Disease of Bone
Pallidopontonigral Degeneration; PPND
Papillary Renal Carcinoma
Paraganglioma
Parkin Type of Juvenile Parkinson Disease
Periodic Paralyses
   Hyperkalemic Periodic Paralysis
   Hypokalemic Periodic Paralysis
     Hypokalemic Periodic Paralysis Type 1
     Hypokalemic Periodic Paralysis Type 2
Potassium-Sensitive Cardiodysrhythmic Type Periodic Paralysis
Periodontitis
Peroxisomal Bifunctional Enzyme Deficiency
Phosphoglycerate Kinase Deficiency
Phosphoglycerate Mutase Deficiency
Phosphorylase Kinase Deficiency of Liver and Muscle
Platelet Antigen Genotyping
PLOSL
Polycystic Kidney Disease
   Polycystic Kidney Disease, Autosomal Dominant Polycystic Kidney Disease 1, Autosomal Dominant
   Polycystic Kidney Disease 2, Autosomal Dominant
   Polycystic Kidney Disease 3, Autosomal Dominant
   Polycystic Kidney Disease, Autosomal Recessive
Porphyria Cutanea Tarda
Potocki-Shaffer Syndrome
Prader-Willi Syndrome
Preeclampsia
Primary Pulmonary Hypertension
Prion Disorders
   Creutzfeldt-Jakob Disease
   Familial Fatal Insomnia
   Gerstmann-Straussler Disease Progressive Familial Intrahepatic Cholestasis
- Progressive Familial Intrahepatic Cholestasis 1
- Progressive Familial Intrahepatic Cholestasis 2

PROP 1-Related Combined Pituitary Hormone Deficiency
Proximal Renal Tubular Acidosis with Ocular Abnormalities
Pseudoachondroplasia
Pseudoneonatal Adrenoleukodystrophy
Pseudovitamin D Deficiency Rickets
Pseudoxanthoma Elasticum
Pulmonary Surfactant Protein B Deficiency
Pycnodysostosis
Pyridoxine-Dependent Seizures
Pyruvoyltetrahydropterin Synthase Deficiency
Red Cell Antigens
- Duffy Antigen Genotyping
- Kell Antigen Genotyping
- Kidd Genotyping
- M Antigen Genotyping
- Rh C Genotyping
- Rh D Genotyping
- Rh E Genotyping
- S Antigen Genotyping Retinitis Pigmentosa
- Retinitis Pigmentosa, Autosomal Dominant
- Retinitis Pigmentosa, Autosomal Recessive Retinitis Pigmentosa, Autosomal Recessive, Bothnia Type
Retinitis Pigmentosa, X-Linked
Retinoblastoma
Rett Syndrome
Rhizomelic Chondrodysplasia Punctata
- Rhizomelic Chondrodysplasia Punctata Type 1
- Rhizomelic Chondrodysplasia Punctata Type 2
- Rhizomelic Chondrodysplasia Punctata Type 3

Rod Monochromacy
Rothmund-Thomson Syndrome
Russell-Silver Syndrome
Saethre-Chotzen Syndrome
Salla Disease
Sclerosteosis
Sex-Determining Region Y
Short Chain 3-Hydroxyacyl-CoA Dehydrogenase Deficiency,
Short Chain Acyl-CoA Dehydrogenase Deficiency
Short Stature
Shox Deficiency
Simpson-Golabi-Behmel Syndrome
Sitosterolemia
Sjogren-Larsson Syndrome
Smith-Magenis Syndrome
Specialized Cytogenetics Services
- Telomere Analysis
- X Inactivation Studies Spinal and Bulbar Muscular Atrophy
Spinal Muscular Atrophy
- Arthrogryposis multiplex congenita
- Congenital axonal neuropathy
- Spinal Muscular Atrophy I
- Spinal Muscular Atrophy II
- Spinal Muscular Atrophy III
- Spinal Muscular Atrophy IV Spinal Muscular Atrophy with Respiratory Distress 1
Split-Hand/Foot Malformation, Type 4
Spondyloepimetaphyseal Dysplasia, Strudwick Type
Spondyloepiphyseal Dysplasia Tarda, X-Linked
Steatocystoma Multiplex
Succinic Semialdehyde Dehydrogenase Deficiency
Sulfatidosis, Juvenile, Austin Type
Thanatophoric Dysplasia Type I
Thanatophoric Dysplasia Type II
Thrombophilia
- Factor V Leiden Thrombophilia
- Factor V R2 Mutation Thrombophilia
- MTHFR Thermolabile Variant
- Prothrombin G20210A Thrombophilia Thyroid Hormone Resistance
Townes-Brocks Syndrome
Transthyretin Amyloidosis
- Familial Amyloid Cardiomyopathy
- Familial Amyloid Polyneuropathy Type 1 (Portuguese-Swedish-Japanese type)
- Familial Amyloid Polyneuropathy Type II (Indiana/Swiss or Maryland/German type)
- Familial Oculoleptomeningeal Amyloidosis
- Leptomeningeal Amyloidosis Trichorhinophalangeal Syndrome Type I Trichothiodystrophy
Tuberous Sclerosis Complex
- Tuberous Sclerosis I
- Tuberous Sclerosis II Type II Collagenopathies
- Achondrogenesis Type II
- Kniest Dysplasia
- Spondyloepiphyseal Dysplasia
- Spondyloepiphyseal Dysplasia, Congenita
- Stickler Syndrome Type I Tyrosinemia Type I
Tyrosinemia Type II
Uniparental Disomy Testing, General
van Buchem Disease
Variegate Porphyria
Very Long Chain Acyl-CoA Dehydrogenase Deficiency
Vohwinkel Syndrome
Von Hippel-Lindau Syndrome
Von Willebrand Disease
- Von Willebrand Disease Type 2A
- Von Willebrand Disease Type 2B
- Von Willebrand Disease Type 2M
- Von Willebrand Disease Type 2N (Normandy)

White Sponge Nevus of Cannon
Williams Syndrome
Wilson Disease
Wiskott-Aldrich Syndrome
Wolf-Hirschhorn Syndrome
Wolman Disease
X-Linked Adrenal Hypoplasia Congenita
X-Linked Agammaglobulinemia
Xeroderma Pigmentosa
Y Chromosome Deletion
- Sertoli Cell Only Syndrome
- Y Chromosome Detection/Molecular Genetics Zellweger syndrome
Zonular Pulverulent Cataract

EXAMPLE 2

Integrated Instrument to Obtain Informed Consent for Genetic Tests for Cystic Fibrosis Genetic testing for cystic fibrosis is now recommended for all Caucasian couples anticipating childbearing. There are currently ~4 million pregnancies/year. Laws in several states require that informed consent be obtained for all genetic tests. Most primary care physicians and OB/GYNs have little training in genetics and limited ability to provide information and instruction to patients concerning genetic tests for cystic fibrosis, the utility and interpretation of test results, the procedures governing genetic testing and genetic information, the social, medical, and psychological implications of testing, and the balance of risk and benefit involved in having such tests performed. The instruments and methods described in this invention enable healthcare practitioners with little training or knowledge of genetics to obtain a meaningful informed consent using validated and integrated elements for providing information and instruction to individuals, collecting a personal medical and family history, assessing the individual's retention and comprehension of information concerning the genetic test, certifying the individual's consent for the test, establishing a proper medical record, and properly processing the sample.

The integrated instrument contains an instruction element which includes stepwise directions to the practitioner in the process of obtaining an informed consent and provides text and illustrative materials that the practitioner can use to explaining the test, the test procedures, and its consequences to the individual. The instrument also to contains text and illustrative materials designed for individuals that constitutes a reliable and understandable source of information about the test. A collection element constitutes a worksheet that can be used by the practitioner and individual to construct a personal medical and family history. The worksheet contains specific questions about the individual's racial make-up, and the racial make-up of the individuals family (siblings, parents, siblings of the parents, grandparents and siblings of the grandparents, and so on), the individual's health status and the health status and history of the individual's family. An assessment element enables the provider to assess the individual's retention of information. It comprises a series of questions about the reasons for the test, the test procedures, the possible test results and the meaning of the test results and basic question about cystic fibrosis. The certification element enables the individual to indicate their permission for testing to be performed and for this permission to be witnessed, it includes a written document that states that the individual has reviewed and understands the information transmitted in the information element and includes blank signature lines for the individual's signature, and the signatures of the practitioner and the witness. Other elements assist in establishing a medical record, labeling the sample, and billing for the cost of the test. The instrument is validated through clinical trials which establish that the language comprising the information element and the procedures established in the instruction element are effective in establishing the requisite level of understanding required for an individual to provide a valid informed consent. Table I below sets forth the contents of an exemplary informed consent instrument for Cystic Fibrosis testing.

EXAMPLE 3

Integrated Instrument to Obtain Informed Consent for Genetic Tests for Alzheimer's Disease Genetic testing for genes involved in Alzheimer's Disease can be performed for individuals with early symptoms of dementia or asymptomatic individuals with a family history of the disease. While Alzheimer's Disease is highly genetic (i.e., it exhibits high heritability) it is also polygenic, meaning many different genes may be involved in its etiology. Genetic tests for variances in apolipoprotein E (apoE4) are associated with a more rapid progression of Alzheimer's disease, and variations in the genes for amyloid precursor protein, antichymotrypsin, and presenillin have also been associated with the disease. The genetics of the disease and determinations of risk based on family history and genetic test results currently requires specialized training in genetics. Most primary care physicians do not have the training to instruct patients in the genetics of Alzheimer's Disease, use of genetic information to assess their risk of Alzheimer's Disease the social, medical, and psychological implications of testing, and the balance of risk and benefit involved in having such tests performed.

The instruments and methods described in this invention enable healthcare practitioners with little training or knowledge of genetics to obtain a meaningful informed consent using validated and integrated elements for providing information and instruction to individuals, collecting a personal medical and family history, assessing the individual's retention and comprehension of information concerning the genetic test, certifying the individual's consent for the test, establishing a proper medical record, and properly processing the sample. These elements comprise a booklet with information about Alzheimer's Disease and the role of genetic testing written at an $8^{th}$ grade level for the patients and give the practitioner stepwise directions and explicit language to use in explaining the genetics of Alzheimer's Disease, diagrams illustrating the natural course of early and late forms of Alzheimer's Disease and the characteristic patterns of inheritance of polygenetic disorders, as well as reference information and answers to frequently asked questions. The instrument also helps the practitioner collect a family history and provides a worksheet that can be used to make a quantitative assessment of genetic risk based on this history. These elements are validated through clinical trials which establish that the language comprising the information element and the procedures established in the instruction element are effective in establishing the requisite level of understanding required for an individual to provide a valid informed consent. Other elements help the provider to assess the individual's retention of information, enable the individual to certify their consent, establish a medical record, label the sample, and arrange payment for the test. Table II below sets forth the contents of an exemplary informed consent instrument for Alzheimer's Disease risk.

EXAMPLE 4

Integrated Instrument to Obtain Informed Consent for Genetic Tests for Risk of Stroke Stroke and other symptomatic manifestations of cardiovascular disease can be caused by several different genetic variations. These different forms of cardiovascular disease may require different therapies. For example, variances in apolipoprotein E, LDL, or LDL-R can lead to increased levels of cholesterol and require therapy with diet and drugs aimed at lowering cholesterol. Variances in methylenetetrahydrofolatereductase may increase levels of homocysteine and require therapy with diet and folate aimed at lowering cholesterol. Variances in the angiotensinogen gene may lead to cardiovascular disease due to imbalances of salt and require therapy with diet, salt restriction, or diuretics aimed at reducing the salt load. Variances in genes involved in the clotting cascade, particularly factor V, may predispose to blood clots and stroke which may be treated with anti-coagulants and anti-thrombotics. Other genetic tests for cardiovascular disease are currently in research and development. To provide informed consent for such tests, the practitioner reviews the patient's family history to make a preliminary calculation of genetic risk and identify likely candidates for such risk (e.g. history of high cholesterol or thrombosis). Based on this information the practitioner may recommend one for more genetic tests that could be used to customize measures to prevent cardiovascular disease and stroke. Most primary care physicians do not have the sufficient training or knowledge of recent developments in cardiovascular genetics to make such determinations and counsel patients in the potential use of genetic information in the prevention of cardiovascular disease.

The instruments and methods described in this invention enable healthcare practitioners with little training or knowledge of genetics to obtain a meaningful informed consent using validated and integrated elements for providing information and instruction to individuals, collecting a personal medical and family history, assessing the individual's retention and comprehension of information concerning the genetic test, certifying the individual's consent for the test, establishing a proper medical record, and properly processing the sample. These elements comprise a booklet with information about the genetic and non-genetic factors that contribute to stroke written at an $8^{th}$ grade level for the patients and give the practitioner stepwise directions and explicit language to use in explaining the genetics of stroke, diagrams illustrating the different factors that contribute to stroke, as well as reference information and answers to frequently asked questions. The instrument also helps the practitioner collect a family history and provides a worksheet that can be used to make a quantitative assessment of genetic risk based on this history. These elements are validated through clinical trials which establish that the language comprising the information element and the procedures established in the instruction element are effective in establishing the requisite level of understanding required for an individual to provide a valid informed consent. Other elements help the provider to assess the individual's retention of information, enable the individual to certify their consent, establish a medical record, label the sample, and arrange payment for the test. The method comprises procuring a booklet that comprises the instrument. The information element is separated from the booklet and given to the patient. The practitioner follows directions in the instruction element to guide the patient through information concerning the ethology of stroke, genetic tests that may be useful in identifying genetic risk factors for stroke, and the process and consequences of performing a test. The practitioner uses a check list to indicate the completion of each step of the process. The practitioner then uses the collection element to collect a personal family and medical history and a worksheet within this element to make a determination of the patient's genetic risk. An assessment of the patient's retention and understanding of the information is made using the assessment instrument, and, when an acceptable level of understanding is demonstrated, the patient signs an informed consent form with witnesses from the certification element according to directions in the instruction element. Carbon copies of the checklist, assessment, and certification are made onto a recording element coincident with the original signatures, and this element is placed in the patient's medical record as described in the instruction element. The sample is labeled with an adhesive backed label that is separated from the back cover of the instrument as described in the instruction element, and the invoice is separated from the instrument and given to the patient. Table III sets forth the contents of an exemplary informed consent instrument for genetic risk of stroke.

EXAMPLE 5

Integrated Instrument to Obtain Informed Consent for Pharmagenogenetic Testing

Genetic variation in genes that are responsible for drug metabolism may alter the safety and efficacy of these medications for an individual. These tests may, for example, identify individuals who are refactory to the pain-killing effects of codeine, individuals who are at risk from undue toxicity from various neuro-psychiatric drugs, and individuals who are at risk of abnormally high levels of warfarin. CYP2D6 and CYP3C9 are two examples of genes that may be tested to help guide the choice of pharmaceutical therapy. Genetic tests for pharmacogenetic testing will commonly be performed by the prescribing physician who may have little or no training in genetics and in situations where professional genetics support may not be available. While the genetic predisposition to adverse drug events or drug resistance may not raise some of the ethical issues that surround genetic tests for disease predisposition, informed consent is, nevertheless, necessary regarding issues such as sample handling, DNA banking, and the privacy of genetic records. Accordingly, physicians need to have an effective method for providing individuals with information concerning the test, how the test results can be used, and how follow-up may be maintained, instructing the individual concerning the handling of the sample and information from the genetic test, and obtaining a valid informed consent.

The instruments and methods described in this invention enable healthcare practitioners with little training or knowledge of genetics to obtain a meaningful informed consent using validated and integrated elements for providing information and instruction to individuals. These elements comprise a booklet with information about genetic effects on drug action and the process of genetic testing written at an $8^{th}$ grade level for the patients and give the practitioner stepwise directions and explicit language to use in explaining how this information could be used to improve the choice of the medication and the dose that will be prescribed. The instrument also contains an assessment to determine the individual's comprehension and retention of information concerning the test and testing procedures. These information element and instruction element also contain materials relating to a follow-up service through which individuals are contacted with regular updates concerning new medications and how these medications are affected by genetic variations. Individuals are asked to indicate their consent for such contacts by the service or to formally reject such contacts in the certification element. The choice whether or not to participate in the follow-up program is also noted in the recording element. If the individual chooses to participate, this element will also include contact information for such follow-up and copies of this element will be recorded automatically with the follow-up service. The billing element is used to pay both for the genetic tests that are to be performed and for an initial subscription to this service. Also included in the instrument are elements for labeling of the sample. Table IV below sets forth the contents of an exemplary informed consent instrument for pharmacogenetic testing.

REFERENCES

Code Of Federal Regulations—§46.116, 46.117

Elias S, Annas G J. Generic consent for genetic screening. N Engl J Med 1994; 330:1611-1613

Andrews L B, Fullarton J E, Holtsman N A, Motuisky A G, eds. Assessing genetic risks: implications for health and social policy. Washington, D.C.: National Academy Press, 1994

Ciske D J, Haavisto A, Laxova A, Rock L Z, Farrell P M. Genetic counseling and neonatal screening for cystic fibrosis: an assessment of the communication process. Pediatrics April 2001; 107(4):699-705

Andrews L B., Compromised consent: deficiencies in the consent process for genetic testing. J Am Med Womens Assoc 1997 Winter; 52(1):39-42

Hofman K J, Tambor E S, Chase G A, Geller G, Faden R R, Holtzman N A., Physicians' knowledge of genetics and genetic tests. Acad Med August 1993; 68(8):625-32

Cho M K, Arruda M, Holtzman N A., Educational material about genetic tests: does it provide key information for patients and practitioners? Am J Med Genet Dec. 19, 1997; 73(3):314-20

Robertson J A., Consent and privacy in pharmacogenetic testing. Nat Genet July 2001; 28(3):207-9

Geller G, Strauss M, Bernhardt B A, Holtzman N A., "Decoding" informed consent. Insights from women regarding breast cancer susceptibility testing. Hastings Cent Rep, March-April 1997; 27(2):28-33

Rieger P T, Pentz R D., Genetic testing and informed consent. Semin Oncol Nurs May 1999; 15(2): 104-15

U.S. Pat. No. 6,149,440 entitled Methods and Apparatus for Authenticating Informed Consent U.S. Pat. No. 5,999,909 entitled Methods for Establishing a Certifiable Informed Consent For A Procedure U.S. Pat. No. 5,799,282 entitled Methods for Establishing Certifiable Informed Consent For A Medical Procedure

TABLE I

INFORMED CONSENT INSTRUMENT FOR CYSTIC FIBROSIS TESTING

| INFORMATION ELEMENT | INSTRUCTION ELEMENT | ASSESSMENT ELEMENT |
|---|---|---|
| What is cystic fibrosis? (PRINTED MATERIALS/ VIDEO PRESENTATION) | Instructions for obtaining informed consent with this product<br>Checklist (WORKSHEET)<br>Instructions to be provided to individuals<br>Instructional materials on cystic fibrosis | 1 Which of the following is not true about CF?<br>(a) CF affects the lungs and digestive system<br>(b) CF is caused by mutations in the CFTR gene<br>(c) there is no treatment for CF<br>(d) CF can cause mild disorders including sterility and chronic sinusitus<br>(e) CF can cause premature death due to lung disease |
| Characteristics of the disease<br>CFTR - the "CF gene" | Describing the characteristics of the disease<br>Describing the biological basis of cystic fibrosis (WITH DIAGRAM) | |
| How is cystic fibrosis inherited? | Describing the inheritance of cystic fibrosis | 2 Which of the following describes the inheritance of CF<br>(a) affected individuals have only one mutant gene which is inherited from the father<br>(b) affected individuas have only one mutant gene which is inherited from the mother<br>(c) cystic fibrosis is caused by an infection with bacteria or viruses<br>(d) affected individuals have two mutant genes. one inherited from each parent |
| Genetic tests for cystic fibrosis | Describing mutations in the CFTR gene and genetic tests | 3. Which of the following is not true of a carrier of CF?<br>(a) carriers are unaffected by cystic fibrosis<br>(b) all of the children of a carrier will be affected with cystic fibrosis<br>(c) on average, 1/4 children of two carriers will be affected with cystic fibrosis<br>(d) on average, 1/2 children of one carrier will also be carriers<br>(e) approximately 1/20 caucasians are carriers |
| What does it mean if I have a gene for cystic fibrosis? | | 4. Which of the following statements are not true?<br>(a) variations in the CFTR gene are the cause of cystic fibrosis<br>(b) approximately 1/20 caucasians are carriers of cystic fibrosis<br>(c) there are fewer carriers of the cystic fibrosis gene among non-caucasians<br>(d) cystic fibrosis never occurs among non-caucasians<br>(e) cystic fibrosis is less common among non-caucasians<br>(f) genetic testing is available to anyone without regard to their race or ancestory |
| Carriers have one mutant gene and one normal gene<br>Affected individuals have two mutant genes<br>What is the treatment for cystic fibrosis? | Describing the carrier status for CF<br>Differentiating carriers from affected individuals<br>Instructional materials on the management of cystic fibrosis | 5 Which of the following statements are not true?<br>(a) early diagnosis and therapy in the newborn period may improve outcome<br>(b) children with CF may suffer from malnutrition and poor growth<br>(c) enzyme and nutritional therapy can restore normal growth<br>(d) treatment with antibiotics can preserve lung function<br>(e) gene therapies to fix the CFTR gene will be approved soon |

TABLE 1-continued

| | |
|---|---|
| Professional healthcare and health management | Describing the role of health care professionals |
| | 6 Which of the following statements are not true? |
| | (a) genetic testing can aid early diagnosis and treatment of affected children |
| | (b) prenatal diagnosis is available to parents who are known to be carriers |
| | (c) abortion is recommended if a child is diagnosed with cystic fibrosis |
| | (d) early diagnosis and treatment of newborns with cystic fibrosis is recommended |
| | (e) two carriers planning a pregnancy should consult with a CF specialist |
| Preventing and treating nutritional problems | Describing enzyme and nutritional management |
| Preventing and treating lung disease | Describing pulmonary management |
| Long term prognosis and quality of life | Describing prognosis for cystic fibrosis |
| Preconception and reproductive planning | Describing prenatal diagnosis and reproductive planning |
| How is the genetic test performed? | Instructional materials on how genetic tests are performed |
| What is informed consent? | Describing the purpose and regulations regarding informed consent |
| | 7 Which of the following statements is not true? |
| | (a) genetic testing can not be performed wihtout your consent |
| | (b) samples are used only for the purpose described in the consent |
| | (c) samples can be sold for research without your consent |
| | (d) samples can be saved for additional testing in the future |
| | (e) a health professional in the laboratory will check the test results |
| | (f) it is recommended to meet with a provider to review test results |
| | (g) your medical records can not be sent to anyone without consent |
| How do I provide a sample for testing? | Describing the testingprocess |
| How is this sample handled? What happens to the sample after the test is completed? | Describing sample handing procedures |
| Who performs the test? | Describing sample testing procedures |
| Who receives the test results? | Describing policies regarding medical record privacy and distribution |
| Does anyone else have to know to know the test results? | Describe the follow-up process |
| How will I know what to do when I receive the test results? | |
| What is genetic counseling? | Describe genetic counseling and referral procedures |
| What does my medical history and family history tell me about my risk? | Instructions on completing medical history and family history |
| Should I have this test performed? | Guiding the individual's choice whether or not to perform a test |
| | 8 Which of the following statements is not true? |
| | (a) You are more likely to be a carrier if someone in your family has cystic fibrosis |
| | (b) You are more likely to be a carrier if someone else in your family is also a carrier |
| | (c) You may carry a CF gene even if no one in your family has ever had the disease |
| | (d) all of the mutations that cause CF can be detected by genetic testing |
| | (e) more than 97% of the mutaitons that cause CF can be detected by genetic testing |
| | (f) genetic testing can be performed before birth through CVS or amniocentesis |
| | (g) generally a child will be affected with CF only if both parents are carriers |
| Does my family history suggest I have an increased risk? | Instructions on calculating risk from family history |
| Recommendations of experts in the field. | Recommendations of the NIH and professional societies |
| | 9 Which of the following statements are true? |
| | (a) genetic testing for carriers of CF is performed at birth by the public health service |
| | (b) the NIH recommends genetic testing for all caucasian couples before childbearing |
| | (c) genetic testing for cystic fibrosis is required by the government and health plans |
| | (d) carriers should not have children because they may have cystic fibrosis |

TABLE 1-continued

| COLLECTION ELEMENT | LABELING ELEMENT |
|---|---|
| Should my family members be tested also? | Guiding a discussion on whether to discuss test with family members |
| What are the benefits of performing this genetic test? | Describing the benefits of identifying genetic risk factors |
| What are the risks of performing this genetic test? | Describing the risks of identifying genetic risk factors |
| Do I want to know this information? | Describing emotional and practical implications of identifying risk factors |
| Will I act on this information? | |
| Will a positive test affect my ability to get a job? | Describing laws against discrimination and nationwide experience |
| Will a positive test affect my ability to get health insurance? | Describing laws against discrimination |
| Will a positive test affect my ability to get life insurance? | Discussing potential impact on life insurance |
| What does it cost? | Pricing and reimbursement issues |
| Instruction on self-assessment | Instructions for performing assessment. |
| Instructions on completing informed consent | Instructions for completing informed consent |
| Instructions for providing a sample | Instructions for obtaining sample |
| | Instructions for labeling sample |
| Is this test covered by my insurance? | Instructions for self-payment or reimbursement |
| Should I pay for this directly? | |
| Should I claim reimbursement? | |
| Who to contact for more information | Instructions for completing medical record |
| Test results | Additional instructional materials |
| Referrals to health care providers | Background on informed consent |
| | Background information on patterns of inheritance (WITH DIAGRAM) |
| | Background information on genes, DNA, chromosomes (WITH DIAGRAM) |
| | Background information on cardiovascular system (WITH DIAGRAM) |
| | Background on psychosocial issues in genetic testing |
| | Background on the potential for genetic discrimination |
| | Answers to frequently asked questions |

10 Which of the following are not prohibited by law?
(a) hiring or firing based on a genetic test result
(b) denying health insurance or health care based on a genetic test
(c) performing a genetic test without an individuals consent
(d) giving test results to employer without an individuals consent
(e) keeping test results secret from employers family or friends

| COLLECTION ELEMENT | CERTIFICATION ELEMENT | LABELING ELEMENT | BILLING ELEMENT | RECORDING ELEMENT |
|---|---|---|---|---|
| | Question 1 result | | | Checklist |
| | Question 2 result | | | Question 1 result |
| | Question 3 result | | | Question 2 result |
| | Question 4 result | | | Question 3 result |
| | | | | Question 4 result |

TABLE 1-continued

| | | | |
|---|---|---|---|
| | Question 5 result | | Question 5 result |
| | Qudestion 6 result | | Qudestion 6 result |
| | Question 7 result | | Question 7 result |
| | | | |
| | Qudstion 8 result | | Qudstion 8 result |
| | Question 9 result | | Question 9 result |
| | Qustion 10 result | | Qustion 10 result |
| Medical and Family History Worksheet | | | |
| Subjective assessment of healthcare concerns | | | |
| Personal medical history | | | |
| Review of systems | | | |
| Family tree/geneology | | | |
| Family medical history | | | |
| | Informed consent form | | |
| | Text | | |
| | Signature pages (duplicate) | | |
| | | Materials for labeling sample | |
| | | Personal identification/deidentification | |
| | | Label to affix to sample | |
| | | Contact information for reporting results | |
| | | | Billing forms |
| | | | self pay forms |
| | | | reimbursement claim forms |
| | | | Checklist for medical record |
| | | | assessment |
| | | | medical history worksheet |
| | | | family history worksheet |
| | | | informed consent (signed) |
| | | | contact information for reporting results |

TABLE II

INFORMED CONSENT INSTRUMENT FOR ALZHEIMER'S DISEASE RISK

| INFORMATION ELEMENT | INSTRUCTION ELEMENT | ASSESSMENT ELEMENT |
|---|---|---|
| | Instructions for obtaining informed consent with this product<br>Checklist (WORKSHEET)<br>Instructions to be provided to individuals | |
| What are the genes that affect my risk for AD? | Instructional materials on pathogenesis of Alzheimer's Disease | 1 Which of the following is not true about Alzheimer's Disease?<br>(a) AD involves the accumulation of amyloid proteins in the brain<br>(b) Dementia is a normal part of the aging process<br>(c) AD is the most common form of dementia<br>(d) The onset of AD is often gradual<br>(e) Most individuals are diagnosed only when the disease is advances<br>(f) The mental deficits caused by AD are not reversible |
| What do these genes do? | Describing the pathology of Alzheimer's Disease (DIAGRAM)<br>Describing the clinical course of Alzheimer's Disease (CHARTS) | |
| How do variations in these genes increase my risk for Alzheimer's Disease? | Describing the inheritance in Alzheimer's Disease | 2 Genetic factors account for what fraction of the risk of stroke?<br>(a) 75-100%<br>(b) 50-75%<br>(c) 25-50%<br>(d) less than 25%<br>(e) none |
| What risk factors can be determined through genetic tests? | Describing the role of specific genes that can be tested | 3 Which of the following genes may be associated with AD?<br>(a) apolipoprotein E (ApoE)<br>(b) Amyloid precursor protein<br>(c) Presenillin<br>(d) antichymotrypsin<br>(e) all of the above |
| What does it mean if I have genes that increase my risk of AD | | 4 Which of the following statements are not true?<br>(a) rare cases of AD are due to severe mutations in single genes<br>(b) most cases are multifactorial or involve multiple genes<br>(c) a positive ApoE test does not mean I will definitely have AD<br>(d) a negative ApoE test means I will definitely not get AD<br>(e) genetic tests may predict the effective of drugs for AD<br>(f) family history is an important medicine of AD risk |
| In rare families, AD is inherited in a predictably genetic manner | | |
| In most families, AD is considered to be multifactorial or associated with many genes | | |
| The effect of ApoE | ApoE | |
| Other genes that may be involved in Alzheimer's Disease Amyloid precursor protein (APP) Presenillin Antichymotrypsin | Amyloid Precursor Protein<br>Presenillin<br>Antichymotrypsin | |
| The effect of combinations of genes | Ongoing research in genetics of Alzheimer's Disease | |

TABLE II-continued

INFORMED CONSENT INSTRUMENT FOR ALZHEIMER'S DISEASE RISK

| | |
|---|---|
| Can I do anything to prevent AD if tests show that I am at risk? | Instructional materials on responding to the risk of Alzheimer's Disease |
| Professional healthcare and health management. | Describing the role of health care professionals |
| Approved drugs delay onset of disease | Describing effect of cholinesterase inhibitors (Tacrine, Aricept, others) |
| Other drugs are being studied in clinical trials | Clinical experience and trials with anti-inflammatory drugs |
| What kind of follow-up and care is available? | Clinical exerience and trials with estrogen |
| | Clinical experience and trials with antioxidants + D11 |
| | Clinical experience and trials with alternative medicines |
| How is the genetic test performed? | Instructional materials on how genetic tests are performed |
| What is informed consent? | Describing the purpose and regulations regarding informed consent |
| How do I provide a sample for testing? | Describing the testingprocess |
| How is the sample handled? What happens to the sample after the test is completed? | Describing sample handing procedures |
| Who performs the test? | Describing sample testing procedures |
| Who receives the test results? | Describing policies regarding medical record privacy and distribution |
| Does anyone else have to know the test results? | |
| How will I know what to do when I receive the test results? | Describe the follow-up process |
| What is genetic counseling? | Describe genetic counseling and referral procedures |
| Should I have this test performed? | Guiding the individual's choice whether or not to perform a test |
| Does my medical history suggest I have an increased risk | Instructions on taking a medical history (WORKSHEET) |
| Does my family history suggest I have an increased risk? | Instructions on taking a family history (WORKSHEET) |
| Recommendations of experts in the field | Recommendations of the NIH and professional societies |
| Should my family members be tested also? | Guiding a discussion on whether to discuss test with family members |

5 Which of the following statements are not true?
  (a) there are no approved drugs for treating or preventing AD
  (b) cholinesterase inhibitors may slow progression of AD
  (c) anti-inflammatory drugs may help prevent AD
  (d) St. Johns Wart has no proven effect on AD
  (e) anti-oxidant drugs may help prevent AD
  (f) behavioral therapy may benefit individuals with AD 6 Which of the following statements are not true?
  (a) genetic testing can help people cope with the risk of AD
  (b) genetic testing can lead to earlier use of drugs to slow AD
  (c) genetic tests today can lead to effective prevention of AD
  (d) follow-up by health professionals is an important part of AD care 7 Which of the following statements is not true?
  (a) genetic testing can not be performed without your consent
  (b) samples are used only for the purpose described in the consent
  (c) samples can be sold for research without your consent
  (d) samples can be saved for additional testing in the future
  (e) a health professional in the laboratory will check the test results
  (f) it is recommended to meet with a provider to review test results
  (g) your medical records can not be sent to anyone without consent 8 Which of the following statement is not true?
  (a) If one or more family members have AD, you have increased risk
  (b) If your father or mother had AD, your risk of AD is >50%
  (c) Genetic tests can not identify all of the risk factors for AD
  (d) Variation in ApoE may increase the rate of progression of AD
  (e) I can be at risk for AD even without a family history of AD
  (f) I can be at risk for a AD even if these tests come back normal TABLE II-continued

INFORMED CONSENT INSTRUMENT FOR ALZHEIMER'S DISEASE RISK

| | |
|---|---|
| What are the benefits of performing this genetic test? | Describing the benefits of identifying genetic risk factors |
| Early detection and prevention of cardiovascular disease | 9 Which of the following statements are true? |
| | (a) genetic testing is recommended for everyone to prevent AD |
| | (b) genetic tests are not recommended without symptoms of AD |
| | (c) a negative genetic test will tell me I am not ar risk for AD |
| | (d) treatments have been shown to effectively prevent most AD |
| | (e) there are no treatments to slow the progression of AD |
| What are the risks of performing this genetic test? | Describing the risks of identifying genetic risk factors |
| | 10 Which of the following are not prohibited by law? |
| | (a) hiring or firing based on a genetic test result |
| | (b) denying health insurance or health care based on a genetic test |
| | (c) performing a genetic test without an individuals consent |
| | (d) giving test results to employer without an individuals consent |
| | (e) keeping test results secret from employers family or friends |
| Do I want to know this information? | Describing emotional and practical implications of identifying risk factors |
| Will a positive test affect my ability to get a job? | Describing laws against discrimination and nationwide experience |
| Will a positive test affect my ability to get health insurance? | Describing laws against discrimination |
| Will a positive test affect my ability to get life insurance? | Discussing potential impact on life insurance |
| What does it cost? | Pricing and reimbursement issues |
| Instructions on self-assessment | Instructions for performing an assessment |
| Instructions on completing informed consent | Instructions for completing informed consent |
| Instructions for providing a sample | Instructions for obtaining sample |
| | Instructions for labeling sample |
| Is this test covered by my insurance? | Instructions for self-payment or reimbursement |
| Should I pay for this directly? | |
| Should I claim reimbursement? | |
| Who to contact for more information | Instructions for completing medical record |
| Test results | Additional instructional materials |
| Referrals to health care providers | Background on informed consent |
| | Background information on patterns of inheritance (WITH DIAGRAM) |
| | Background information on genes DNA, chromosomes (WITH DIAGRAM) |
| | Background information on cardiovascular system (WITH DIAGRAM) |
| | Background on psychosocial issues in genetic testing |
| | Background on the potential for genetic discrimination |
| | Answers to frequently asked questions |

| COLLECTION ELEMENT | CERTIFICATION ELEMENT Checklist | LABELING ELEMENT | BILLING ELEMENT | RECORDING ELEMENT Checklist |
|---|---|---|---|---|
| | Question 1 result | | | Question 1 result |
| | Question 2 result | | | Question 2 result |
| | Question 3 result | | | Question 3 result |
| | Question 4 result | | | Question 4 result |
| | Question 5 result | | | Question 5 result |

TABLE II-continued

INFORMED CONSENT INSTRUMENT FOR ALZHEIMER'S DISEASE RISK

| | |
|---|---|
| | Question 6 result |
| | Question 7 result |
| | Question 8 result |
| | Question 9 result |
| | Question 10 result |
| Medical and Family History Worksheet | |
| Subjective assessment of healthcare concerns | |
| Personal medical history | |
| Review of systems | |
| Family tree/geneology | |
| Family medical history | |
| | Question 6 result |
| | Question 7 result |
| | Question 8 result |
| | Question 9 result |
| | Qustion 10 result |
| Informed consent form | |
| Text | |
| Signature pages (duplicate) | |
| | Materials for labeling sample |
| | Personal identification/deidentification label to affix to sample |
| | Contact information for reporting results |
| | Billing forms |
| | self pay forms |
| | reimbursement claim forms |
| | Checklist for medical records assessment |
| | medical history worksheet |
| | family history worksheet |
| | informed consent (signed) |
| | contact information for reporting results |

TABLE III

INFORMED CONSENT INSTRUMENT FOR RISK OF STROKE

| INFORMATION ELEMENT | INSTRUCTION ELEMENT<br>Instructions for obtaining informed consent with this product<br>Checklist (WORKSHEET)<br>Instructions to be provided to individuals | ASSESSMENT ELEMENT |
|---|---|---|
| What are the genes that affect my risk for stroke? | Instructional materials on the pathogenesis of stroke | 1 Which of the following is not true about stroke?<br>(a) stroke involves a temporary loss of blood flow to part of the brain<br>(b) strokes are generally associated with diseases of blood vessels<br>(c) strokes do not occur in people less than 50 years of age<br>(d) high blood pressure can increase the risk of stroke<br>(e) increased blood clotting can increase the risk of stroke<br>(e) the risk of stroke can be decreased by lifestyle diet and drugs |
| What do these genes do?<br>How do variations in these genes increase my risk for stroke? | Describing the biological basis of stroke (WITH DIAGRAM)<br>Describing the role of genetics in stroke | 2 Genetic factors account for what fraction of the risk of stroke?<br>(a) 100%<br>(b) more than 75%<br>(c) 30-50%<br>(d) less than 25% |
| What risk factors can be determine through genetic tests? | Describing the role of specific genes that can be tested | 3 Which of the following genes may be involved in the risk of stroke?<br>(a) apolipoprotein E (ApoE(<br>(b) methylenetetrahydrofolate reductase (MTHFR)<br>(c) blood clotting factors (factor V)<br>(d) angiotensinogen<br>(e) all of the above |
| What does it mean if I have genes that increase my risk for stroke? | | 4 Which of the following statements are not true?<br>(a) all of the genes that predict the risk of stroke are known<br>(b) approximately 10% of normal people have variations in MTHFR<br>(c) complete genetic deficiency of LDL-R is very rare<br>(d) variations in angiotensinogen may lead to high blood pressure<br>(e) some variations in ApoE prevent stroke, others increase the risk<br>(f) genetic variations may increase the risk of blood clots in the brain |
| The effect of genes that predispose to high blood pressure<br>The effect of genes that predispose to blood clotting<br>The effect of genes that increase cholesterol, homocysteine, or blood sugar (diabetes)<br>The effect of combinations of genes<br>What can I do to prevent a stroke if the test shows I have an increased risk? | Angiotensinogen<br>Factor V, factor II<br>ApoE, LDL-R, LPL, MTHFR<br><br>Describing polygenic or multifactorial disease<br>Instructional materials on options to reduce the risk of stroke | 5 Which of the following statements are not true?<br>(a) lowering blood pressure reduces the risk of stroke<br>(b) lowering cholesterol and homocysteine reduces the risk of stroke<br>(c) treating diabetes early lowers the risk of stroke<br>(d) the genetic risk of stroke can not be reduced by diet or drugs<br>(e) the risk of stroke is related to several genes diet and lifestyle |

TABLE III-continued

INFORMED CONSENT INSTRUMENT FOR RISK OF STROKE

| | |
|---|---|
| Professional healthcare and health management | Describing the role of health care professionals |
| | 6 Which of the following statements are not true? |
| | (a) dietary changes can lower cholesterol and the risk Of stroke |
| | (b) a diet rich in folate and vitamin B12 may reduce the risk of stroke |
| | (c) drugs that lower cholesterol may reduce the risk of stroke |
| | (d) anyone at risk for stroke should take drugs to inhibit blood clotting |
| | (e) controlling diabetes reduces the risk of stroke |
| Lifestyle changes | Describing the role of lifestyle changes |
| Dietary changes and supplements | Describing dietary restriction and supplements |
| Drugs to control blood pressure | Describing the treatment of elevated blood pressure |
| Drugs to control cholesterol and triglycerides | Describing the treatment of elevated cholesterol and triglycerides |
| Drugs to prevent blood clots | Describing drugs to prevent thrombosis |
| Preventing and treating diabetes | Describing the diagnosis and treatment of diabtestes |
| How is the genetic test performed? | Instructional materials on how genetic tests are performed |
| What is informed consent? | Describing the purpose and regulations regarding informed consent |
| | 7 Which of the following statements is not true? |
| | (a) genetic testing can not be performed without your consent |
| | (b) samples are used only for the purpose described in the consent |
| | (c) samples can be sold for research without your consent |
| | (d) samples can be saved for additional testing in the future |
| | (e) a health professional in the laboratory will check the test results |
| | (f) it is recommended to meet with a provider to review test results |
| | (g) your medical records can not be sent to anyone without consent |
| How do I provide a sample for testing? | Describing the testingprocess |
| How is this sample handled? What happens to the sample after the test is completed? | Describing sample handing procedures |
| Who performs the test? | Describing sample testing procedures |
| Who receives the test results? | Describing poicies regarding medical record privacy and distribution |
| Does anyone else have to know to know the test results? | |
| How will I know what to do when I receive the test results? | Describe the follow-up process |
| What is genetic counseling? | Describe genetic counseling and referral procedures |
| Should I have this test performed? | Guiding the individual's choice whether or not to perform a test |
| | 8. Which of the following statement is not true? |
| | (a) If two or more family members had strokes, you have increased risk |
| | (b) If your father or mother had a stroke, your risk of a stroke is >90% |
| | (c) Genetic tests can not identify all of the risk factors for stroke |
| | (d) Variation in ApoE, MTHFR, or fator V can increase the risk of stroke |
| | (e) I can be at risk for stroke even without a family history of stroke |
| | (f) I can be at risk for a stroke even if these tests come back normal |
| Does my medical history suggest I have increased risk | Instructions on taking a medical history (WORKSHEET) |
| Does my family history suggest I have an increased risk? | Instructions on taking a family history (WORKSHEET) |
| Recommendations of experts in the field. | Recommendations of the NIH and professional societies |
| Should my family members be tested also? | Guding a discussion on whether to discuss test with family members |

TABLE III-continued

INFORMED CONSENT INSTRUMENT FOR RISK OF STROKE

| | |
|---|---|
| What are the benefits of performing this genetic test? | Describing the benefits of identifying genetic risk factors |
| Early detection and prevention of cardiovascular disease | |
| | 9 Which of the following statments are true? |
| | (a) genetic testing is recommended for everyone to prevent storke |
| | (b) genetic tests identify all of the risk factors for stroke |
| | (c) genetic testing can be used to help reduce the risk of stroke |
| | (d) genetic testing can tell me if I am not ar risk for a stroke |
| | (e) genetic testing is essential to prevent stroke |
| What are the risks of performing this genetic test? | Describing the risks of identifying genetic risk factors |
| | 10 Which of the following are not prohibited by law? |
| | (a) hiring or firing based on a genetic test result |
| | (b) denying health insurance or health care based on a genetic test |
| | (c) performing a genetic test without an individuals consent |
| | (d) giving test results to employer without an individuals consent |
| | (e) keening test results secret from employers family or friends |
| Do I want to know this information? | Describing emotional and practical implications of identifying risk factors |
| Will a positive test affect my ability to get a job? | Describing laws against discrimination and nationwide experience |
| Will a positive test affect my ability to get health insurance? | Describing laws against discrimination |
| Will a positive test affect my ability to get life insurance? | Discussing potential impact on life insurance |
| What does it cost? | Pricing and reimbursement issues |
| Instruction on self-assessment | Instructions for performing assessment |
| Instruction on completing informed consent | Instructions for completing informed consent |
| Instruction for providing a sample | Instructions for obtaining sample |
| | Instructions for labeling sample |
| Is this test covered by my insurance? | Instructions for self-payment or reimbursement |
| Should I pay for this directly? | |
| Should I claim reimbursement? | |
| | Instructions for completing medical record |
| | Additional instructional materials |
| Who to contact for more information | Background on informed consent |
| Test results | Background information on patterns of inheritance (WITH DIAGRAM) |
| Referrals to health care providers | Background information on genes, DNA, chromosomes (WITH DIAGRAM) |
| | Background information on cardiovascular system (WITH DIAGRAM) |
| | Background on psychosocial issues in genetic testing |
| | Background on the potential for genetic discrimination |
| | Answers to frequently asked questions |

| COLLECTION ELEMENT | CERTIFICATION ELEMENT Checklist | LABELING ELEMENT | BILLING ELEMENT | RECORDING ELEMENT Checklist |
|---|---|---|---|---|
| | Question 1 result | | | Question 1 result |
| | Question 2 result | | | Question 2 result |
| | Question 3 result | | | Question 3 result |

TABLE III-continued

INFORMED CONSENT INSTRUMENT FOR RISK OF STROKE

|  |  |  |
|---|---|---|
|  | Qustion 4 result h | Qustion 4 result |
|  | Quesxtion 5 result | Quesxtion 5 result |
|  | Question 6 result | Question 6 result |
|  | Question 7 result | Question 7 result |
|  | Question 8 result | Question 8 result |
| Medical and Family History Worksheet |  |  |
| Subjective assessment of healthcare concerns |  |  |
| Personal medical history |  |  |
| Review of systems |  |  |
| Family tree/geneology |  |  |
| Family medical history |  |  |
|  | Question 9 result | Question 9 result |
|  | Question 10 result | Question 10 result |
|  | Informed content form |  |
|  | Text |  |
|  | Signature pages (duplicate) |  |
|  | Materials for labeling sample |  |
|  | Personal identification/deidentification |  |
|  | Label to affix to sample |  |
|  | Contact information for reporting results |  |
|  | Billing forms |  |
|  | self pay forms |  |
|  | reimbursement claim forms |  |
|  |  | Checklist for medical records assessment |
|  |  | medical history worksheet |
|  |  | family history worksheet |
|  |  | informed consent (signed) |
|  |  | contact information for reporting results |

TABLE IV

INFORMED CONSENT FOR PHARMACOGENETIC TESTING

| INFORMATION ELEMENT | INSTRUCTION ELEMENT | ASSESSMENT ELEMENT |
|---|---|---|
| | Why informed consent is an important part of genetic testing | |
| | Instructions on use of this instrument for patient instruction | |
| | Instructions on use of this instrument for informed consent | |
| | Checklist (shorksheet) | |
| | Instructions to be provided to individuals | |
| How my genes may affect the safety and effectiveness of the drugs I take | Instructional materials on genetic affects on drug action | 1 Which of the following ARE NOT true? (a) Durgs may have different effects in different people (b) My response to a drug may be affected by my genes (c) Drugs approved by the FDA are always safe (d) The safety of a drug I take may be affected by my genes (e) The effectiveness of a drug I take may be affected by my genes |
| Genes may affect how drugs are taken up and activated in my body | Describing genetic effects on ADME (text and diagram) | 2 Which of the following ARE NOT true about genetic tests for drug safety and effectiveness? (a) Tests can predict how quickly my body can break down certain drugs |
| Genes may affect how drugs are activated in my body | Describing the effect of genetic variation in the target of drug action | (b) Tests can predict how quickly my body can activate certain drugs (c) Tests can tell me whether all the drugs I take are safe and effective |
| Genes may affect how a certain drug works for me | Describing the association of certain genes with specific drug toxicities | (d) Tests can help my doctor choose a drug and dose that is right for me |
| Genes may affect how drugs are broken down and eliminated from my body | | (e) Tests can help me and my doctor avoid drug interactions |
| Genes may determine whether a scertain drug is particularly risky for me | | |
| What is genetic variation? Why is is relevant to drug action? | Instructional materials on genetic variation | 3 Which of the following ARE true about genetic tests (a) Genetic tests only identify mutations that cause genetic disease |
| Everyone's genes contain variations | Normal genetic variation | (b) Since I have always been healthy, I don't have any genetic variations |
| Some variations may cause disease | The concept of mutation and normal polymorphism | (c) If I have not been exposed to carcinogenes or radition, I probably don't have any variations |
| | Patterns of inheritance | (d) Everyone has thousands of genetic variations that may affect health |
| Most variations are normal and contribute to our individuality | | (e) If my family members do not have drug toxicity, I don't have to worry |
| Genetic variations is inherited but may not be apparent in every person | Variable expression in different individuals and gneerations | |
| How can information from a genetic test be used to improve my care | Instructional materials on the application of test results | 4 Which of the following ARE NOT true about how my doctor may use the genetic test result? (a) My doctor may use the results to choose among different drugs for treating my disease |
| How my doctor can use information from a genetic test to choose drugs that are most likely to be safe and effective for me | How physicians can use test results to choose appropriate therapies | (b) My doctor may alter the dose of a drug that is customized for my needs |
| | Choosing alternative drugs from a class of drugs | (c) My doctor may avoid giving me certain drugs |
| | Choosing the appropriate dose and form of the drug | (d) My doctor will be able to guarantee that the drugs which are prescribed are safe |
| | Monitoring drug levels and effect | (e) My doctor may choose to monitor the level of a drug in my blood |
| How I can use the information from a genetic test to avoid drug sensitivities and toxicity | Improving compliance with prescribed drugs | 5 Which of the following ARE NOT true about how I will be able to use the genetic test results (a) Inform my doctor that I have had the test before receiving any prescription |
| | Care in choosing over the counter medications | (b) Be aware of potential sensitives to certain drugs |
| | Care in the use of herbal remedies | (c) Take a smaller dose of all drugs to be sure they are safe |
| | Care in choice of diet | (d) Avoid certain over-the-counter medicines or herbal remedies |
| | | (e) Watch certain elements of my diet |

TABLE IV-continued

INFORMED CONSENT FOR PHARMACOGENETIC TESTING

| | |
|---|---|
| What does my medical history and family history tell me about my risk? My history of previous drug use, sensitivity, or toxicity Family history of drug sensitivity or toxicity How is a genetic test performed | Instructions on completing medical history and family history<br><br>Instructional materials on how genetic tests are peformed |
| What is informed consent? | Describing the purpose and regulations regarding informed consent |
| | 6 Which of the following ARE NOT generally considered steps in performing a genetic test?<br>(a) Obtaining a sample from a cheek swab or blood sample<br>(b) Sending the sample to a laboratory<br>(c) Extracting DNA from a sample<br>(d) Storing DNA from the sample<br>(e) Inserting new genetic materials into a sample<br>(f) Reporting restuls of the test to the subject<br>(g) Reporting results of the rest to the referring physician |
| How do I provide a sample for testing? | Describing the testingprocess |
| How is this sample handled? What happens to the sample after the test is completed? | Describing sample handing procedures |
| Who performs the test? | Describing sample testing procedures |
| Who receives the test results? | Describing policies regarding medical record privacy and distribution |
| Does anyone else have to know the test results? | |
| | 7 Which of the following statements ARE NOT true?<br>(a) genetic testing can not be performed without your consent<br>(b) samples are used only for the purpose described in the consent<br>(c) samples can be sold for research without your consent<br>(d) samples can be saved for additional testing in the future<br>(e) a health professional in the laboratory will check the test results<br>(f) it is recommended to meet with a provider to review test results<br>(g) your medical records can not be sent to anyone without consent |
| How will I know what to do when I receive the test results? | Describe the follow-up process |
| What is genetic counseling? | Describe genetic counseling and referral procedures |
| Why is follow-up very important? | Describe importance of follow-up and proceedures |
| Should I have this test performed? | Guiding the individual's choice whether or not to perform a test |
| | 8. Which of the following statements ARE NOT true?<br>(a) Many durg sensitivities are due to genetic variations<br>(b) If my relatives have had drug sensitivities or toxicity, I am more likely to have these also<br>(c) If no one in my family has a history of drug sensitivity or toxicity, I don't need to worry<br>(d) If I tend to be sensitive to drugs, it is possible this sensitivity is due to a genetic effect<br>(e) Genetic tests can not guarantee that every drug I take will be safe or effective<br>(f) If I have genetic variations causing drug sensitivity, my relatives may have the same variations |
| Does my medical history or family history indicate an increased risk Am I taking drugs, or am I likely to take drugs affected by genetic variation | Instructions on predicing risk from medical/ family history |

TABLE IV-continued

INFORMED CONSENT FOR PHARMACOGENETIC TESTING

| | |
|---|---|
| Recommendation of experts in the field | Recommendations of the NIH risk and professional societies |
| | 9 Which of the following ARE NOT true about genetic tests to identify variations in 2D6? |
| | (a) ~5-10% of all individuals in the US have variations in 2D6 that may affect drug action |
| | (b) Variations in 2D6 tht affect drug action are less common in African Americans |
| | (c) Any potential variation in 2D6 can be detected by genetic testing |
| | (d) Variations in 2D6 may make codeine an ineffective medicine for some people |
| | (e) Variations in 2D6 may alter my response to certain drugs for anxiety or depression |
| | (f) Variations in 2D6 may alter my response to some over the counter medicines |
| Should my family members be tested also? | Guiding a discussion on whether to discuss test with family members |
| What are the benefits of performing this genetic test? | Describing the benefits of identifying genetic risk factors |
| What are the risks of performing this genetic test? | Describing the risks of identifying genetic risk factors |
| | 10 Which of the following ARE NOT prohibited by law? |
| | (a) hiring or firing based on a genetic test result |
| | (b) denying health insurance or health care based on a genetic test |
| | (c) performing a genetic test without an individuals consent |
| | (d) giving test results to employer without an individuals consent |
| | (e) keeping test results secret from employers, family, or friends |
| Do I want to know this information? | Describing emotional and practical implications of identifying risk factors |
| Will I act on this information? | |
| Will a positive test affect my ability to get a job? | Describing laws against discrimination and nationwide experience |
| Will a positive test affect my ability to get health insurance? | Describing laws against discrimination |
| Will a positive test affect my ability to get life insurance? | Discussing potential impact on life insurance |
| What does it cost? | Pricing and reimbursement issues |
| Instruction on self-assessment | Instructions for performing assessment |
| | Corect answers to assessment |
| | Instructions for scoring assessment |
| | Instructions for further instruction and assessment |
| Instructions on completing informed consent | Instructions for completing informed consent |
| Instructions for providing a sample | Instructions for obtaining sample |
| | Instructions for labeling sample |
| Is this test covered by my insurance? | Instructions for self-payment or reimbursement |
| Should I pay for this directly? | |
| Should I claim reimbursement? | |
| Who to contact for more information | Instructions for completing medical record |
| Test results | Additional instructional materials |
| Referrals to health care providers | Background on informed consent |
| Long-term follow-up about new tests and new drugs | Tables of genetic effects on commonly used drugs |
| | Background information on patterns of inheritance (WITH DIAGRAM) |
| | Background information on genes, DNA, chromosomes (WITH DIAGRAM) |
| | Background on psychosocial issues in genetic testing |
| | Background on the potential for genetic discrimination |
| | Answers to frequently asked questions |

TABLE IV-continued

INFORMED CONSENT FOR PHARMACOGENETIC TESTING

| COLLECTION ELEMENT | CERTIFICATION ELEMENT Checklist | LABELING ELEMENT | BILLING ELEMENT | RECORDING ELEMENT Checklist |
|---|---|---|---|---|
| | Question 1 result | | | Question 1 result |
| | Qustion 2 result | | | Question 2 result |
| | Quedstion 3 result | | | Question 3 result |
| | Question 4 result | | | Question 4 result |
| | Question 5 result | | | Question 5 result |
| Medical and Family History Worksheet | | | | Medical and Family History Worksheet |
| Personal medical History | | | | Personal medical history |
| History of drug sensitivity or toxicity | | | | History of drug sensitivity or toxicity |
| Review of systems | | | | Review of systems |
| Family tree/geneology | | | | Family tree/geneology |
| Family medical history | | | | Family medical history |
| | Question 6 result | | | Quedstion 6 result |
| | Question 7 result | | | Question 7 result |
| | Question 8 result | | | Question 8 result |
| | Question 9 result | | | Question 9 result |
| | Question 10 result | | | Question 10 result |
| | Assessment score | | | Assessment score |
| | Informed consent form | | | |
| | Text | | | |
| | Signature pages (duplicate) | | | |
| | | Materials for labeling sample | | |
| | | Personal identification/deidentification | | |
| | | Label to affix to sample | | |
| | | Contact information for reporting results | | |
| | | | Billing forms | |
| | | | self pay forms | |
| | | | reimbursement claim forms | Checklist for medical record assessment |
| | authorization for information release | | | medical history worksheet |
| | | | | family history worksheet |
| | | | | informed consent (signed) |
| | | | | contact information for reporting results |
| | consent for long-term follow-up | | | contact information for follow-up |

I claim:

1. A kit, comprising:
   an instrument embodied on a computer recordable medium for obtaining from an individual informed consent prior to conducting a genetic test on said individual, said instrument comprising:
   (a) an information element, wherein said information element comprises information required for obtaining the individuals about the genetic test;
   (b) an instruction element, integrated with said information element, wherein said instruction element comprises directions on how to instruct the individual in the information in the information element;
   (c) a certification element, integrated with said instruction and said information elements; and
   (d) an assessment element, integrated with said information and said instruction elements, wherein said assessment element comprises text questions covering information presented in the information element and instruction element;
   wherein said information element, instruction element, certification element and assessment element is each through a virtual provider.

2. A kit according to claim 1 wherein said genetic test is selected from the group consisting of a test for one gene, a test for more than one gene, a test for related genes, a test for genes associated with a specified clinical outcome and a gene screen test.

3. A kit according to claim 1 comprising at least one additional element selected from the group consisting of a collection element, a labeling element, a billing element, a recording element, a training element, a quality control element, and an indemnification element, wherein said additional element interacts with said individual through a virtual provider.

4. A kit according to claim 3 wherein said additional element comprises a collection element.

5. A kit according to claim 4, additionally comprising at least one element selected from the group consisting of a labeling element, a billing element, a recording element, a training element, a quality control element and an indemnification element.

6. The kit according to claim 1 wherein said instruction element comprises a checklist.

7. The kit according to claim 1 wherein said assessment element comprises questions about one or more of the following selected from the group consisting of the genetic test, the risks and benefits of the genetic test, clinical practice guidelines, recommendations, and possible clinical actions in response to the genetic test results.

8. The kit according to claim 7 wherein the assessment element further comprises answers to each of the questions and procedures for responding to incorrect questions answers.

9. The kit according to claim 1 wherein the questions covering information presented in the information element and instruction element concern a genetic test for one gene, more than one gene, related genes, a clinical outcome or a gene screen to be performed, possible test results, DNA banking, the medical significance of potential test results, standard of care recommendations concerning such tests, the choices available based on the test results, the specific benefits and risks of performing the tests, the procedure for obtaining a sample and performing a test, the disposition and potential future use of the sample as well as the test results, guidelines for protecting the privacy and confidentiality of the individual, and legal issues regarding liability.

10. A method for obtaining through a virtual provider informed consent from an individual prior to conducting a genetic test on said individual, comprising the steps of:
    (a) conveying to the individual information concerning said genetic test using an information element of an integrated instrument embodied on a computer recordable medium for obtaining informed consent to the genetic test, said instrument including an information element, an instruction element integrated with said information element, a certification element integrated with said information and said instruction elements; and an assessment element, integrated with said information and said instruction elements,
       (i) wherein said information element comprises information required for obtaining the individual's consent for the genetic test,
       (ii) wherein said instruction element directs the virtual provider on how to instruct the individual as to the information in the information element, and
       (iii) wherein said assessment element comprises text questions covering information in said information element and said instruction element to assess the individual's understanding of the test to be performed;
    (b) instructing the individual according to the directions contained in said instruction element;
    (c) certifying the individual's consent for said test using said certification element;
    (d) assessing the individual's retention and comprehension of the information concerning the genetic test using said assessment element; and optionally
    (e) obtaining a sample from the individual and performing said genetic test on said sample to obtain a result;
    wherein at least steps (a)-(d) are facilitated through a virtual provider.

11. The method according to claim 10, wherein said integrated instrument additionally includes a virtual provider collection element integrated with said information and said instruction elements, and said method comprises the additional step of collecting a personal medical history and family history using said collection element.

12. The method according to claim 10 wherein said integrated instrument additionally includes a virtual provider labeling element integrated with said information and said instruction elements, and said method includes the additional step of labeling a sample with the identity of the individual using said labeling element.

13. The method according to claim 10 wherein said integrated instrument additionally includes a virtual provider recording element integrated with said information and said instruction elements, and said method includes the additional step of recording information concerning the informed consent process using said recording element.

14. The method according to claim 10 wherein said genetic test is selected from the group consisting of a test for one gene, a test for more than one gene, a test for related genes, a test for genes associated with a specified clinical outcome and a gene screen test.

15. The method according to claim 10 wherein said assessment element comprises questions about one or more of the following pieces of information selected from the group consisting of the genetic test, the risks and benefits of the genetic test, clinical practice guidelines, recommendations, and possible clinical actions in response to the genetic test results.

16. The method according to claim 15 wherein the questions in the assessment element concern content from the information element and the instruction element, and wherein the assessment element further comprises answers to each of the questions and procedures for responding to incorrect answers.

17. The method according to claim 10 wherein the assessment element includes text comprising questions covering information presented in the information element and instruction element concerning a genetic test for one gene, more than one gene, related genes, a clinical outcome or a gene screen to be performed, possible test results, DNA banking, the medical significance of potential test results, standard of care recommendations concerning such tests, the choices available based on the test results, the specific benefits and risks of performing the tests, the procedure for obtaining a sample and performing a test, the disposition and potential future use of the sample as well as the test results, guidelines for protecting the privacy and confidentiality of the individual, and legal issues regarding liability.

* * * * *

UNITED STATES PATENT AND TRADEMARK OFFICE
CERTIFICATE OF CORRECTION

| | | |
|---|---|---|
| PATENT NO. | : 8,438,042 B2 | Page 1 of 1 |
| APPLICATION NO. | : 10/134424 | |
| DATED | : May 7, 2013 | |
| INVENTOR(S) | : Ledley | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2482 days.

Signed and Sealed this
Thirtieth Day of December, 2014

Michelle K. Lee
*Deputy Director of the United States Patent and Trademark Office*